(12) United States Patent
Siochi

(10) Patent No.: US 6,353,655 B1
(45) Date of Patent: Mar. 5, 2002

(54) SYSTEM AND METHOD FOR CALCULATING FLUENCE CONTRIBUTIONS FROM A SOURCE PLANE

(75) Inventor: Ramon Alfredo Carvalho Siochi, Apex, NC (US)

(73) Assignee: Siemens Medical Solutions, Inc., Iselin, NJ (US)

( * ) Notice: Subject to any disclaimer, the term of this patent is extended or adjusted under 35 U.S.C. 154(b) by 0 days.

(21) Appl. No.: 09/648,193

(22) Filed: Aug. 23, 2000

(51) Int. Cl.[7] .................................................. A61N 5/10
(52) U.S. Cl. .......................................... 378/65; 378/62
(58) Field of Search .............................. 378/65, 62, 64, 378/68

(56) References Cited

U.S. PATENT DOCUMENTS

| | | | |
|---|---|---|---|
| 5,608,874 A | 3/1997 | Ogawa et al. ......... | 395/200.15 |
| 5,663,999 A | 9/1997 | Siochi ........................... | 378/65 |
| 5,724,403 A | 3/1998 | Siochi et al. ................ | 378/150 |
| 6,097,787 A * | 8/2000 | Siochi .......................... | 378/65 |
| 6,108,400 A * | 8/2000 | Siochi .......................... | 378/65 |
| 6,167,114 A * | 12/2000 | Siochi ........................... | 37/65 |

* cited by examiner

Primary Examiner—Robert H. Kim
Assistant Examiner—Irakli Kiknadze

(57) ABSTRACT

A method for calculating fluence contributions for radiation delivery from a source to a treatment area through an aperture. The method includes defining a calculation plane located adjacent to said treatment area and a scattering plane located between the radiation source and the calculation plane. A source plane located between the radiation source and scattering plane is also defined. The method further includes ray tracing a point located on the calculation plane to the scattering plane to define a scatter strip and projecting the scatter strip from the scattering plane to the source plane to define a rectangular region. An area integration is performed on the region to determine a fluence value for the rectangular region.

13 Claims, 24 Drawing Sheets

SYSTEM AND METHOD FOR CALCULATING FLUENCE CONTRIBUTIONS FROM A SOURCE PLANE

FIELD OF THE INVENTION

The invention relates to a radiation emitting device, and more particularly to a system and method for calculating scatter radiation of the radiation emitting device.

BACKGROUND OF THE INVENTION

Radiation emitting devices are generally known and used, for instance, as radiation therapy devices for the treatment of patients. A radiation therapy device usually includes a gantry which can be swiveled around a horizontal axis of rotation in the course of therapeutic treatment. A linear accelerator is typically located in the gantry for generating a high-energy radiation beam for therapy. This high-energy radiation beam can be an electron radiation or photon (x-ray) beam. During treatment, this radiation beam is typically trained on a zone of a patient lying in the isocenter of the gantry rotation.

In order to provide a proper dose of radiation to a patient, a dose chamber may be used. A dose chamber accumulates dose deliveries from the radiation beam. When the dose of the radiation beam reaches a given number of counts, then the radiation beam may be turned off. The unit with which the dose chamber counts is a "monitor unit". Determining how many monitor units to set the dose chamber so that the patient receives a proper dose is typically termed as dosimetry. Once a dose for a patient is determined, this dose typically needs to be translated into monitor units. There may be several factors in translating the dose into monitor units, such as attenuation through the patient, accounting for curvature of patient surface, and accounting of scattered radiation inside the patient.

In determining a dose to a patient, a hypothetical plane, often referred to as a calculation plane, a patient plane, or an isocentric plane, directly above the patient may be used in determining the distribution of radiation intensity over the patient. The unit of measurement for radiation intensity is fluence, which is the number of photons per area per time. This calculation plane over the patient may be divided into squares, herein referred to as calculation squares. In determining the fluence over the calculation plane, only one calculation square above the immediate target is typically calculated for the fluence due to the complication of calculating fluence over all of the squares in the calculation plane.

A problem with calculating the fluence in only one calculation square is that the approximation for the remaining calculation squares may be inaccurate. In particular, in the field of intensity modulation, this type of approximation for fluence of the calculation plane may be wholly inadequate. Intensity modulation typically improves the ratio of radiation dose to critical structures versus dose to target. Improving this ratio is highly desirable since it is assumed that non-target areas are receiving radiation. A common goal is to maximize the radiation dose to a target, such as the tumor, while minimizing the radiation dose to healthy tissue.

Another method for calculating the fluence over the calculation plane attempts to calculate the fluence over each calculation square by using ray tracings through a thin aperture. A potential problem with this conventional calculation is that the volume of ray tracing calculations are typically substantial and a substantial amount of processing power is required. Additionally, a radiation aperture, such as a collimator, typically has enough of a thickness to effect the calculations. Accordingly, calculating with the assumption that the aperture is very thin may result in errors.

It would be desirable to have a method for calculating the fluence over the calculation plane which is fast, efficient, and accurate. The present invention addresses such a need.

SUMMARY OF THE INVENTION

The present invention relates to an efficient method and system for calculating fluence of a calculation plane over a patient. In one embodiment, a method of the present invention is for calculating fluence contributions for radiation delivery from a source to a treatment area through an aperture. The method includes defining a calculation plane located adjacent to said treatment area and a scattering plane located between the radiation source and the calculation plane. A source plane located between the radiation source and scattering plane is also defined. The method further includes ray tracing a point located on the calculation plane to the scattering plane and projecting the scatter strip from the scattering plane to the source plane to define a rectangular region. An area integration is performed on the rectangular region to determine a fluence value for the element.

In another aspect of the invention, a system generally comprises a processor configured to ray trace a point from a calculation plane located adjacent to said treatment area to a scattering plane to define a plurality of scatter strips, project the scatter strips onto a source plane located between the radiation source and scattering plane to define a plurality of scatter elements corresponding to said plurality of scatter strips, and calculate area integrations for each of said scatter elements. The system further includes a memory coupled with the processor and configured to provide instruction to the processor.

The above is a brief description of some deficiencies in the prior art and advantages of the present invention. Other features, advantages, and embodiments of the invention will be apparent to those skilled in the art from the following description, drawings, and claims.

DETAILED DESCRIPTION OF THE PREFERRED EMBODIMENTS

The following description is presented to enable one of ordinary skill in the art to make and to use the invention and is provided in the context of a patent application and its requirements. Various modifications to the preferred embodiments will be readily apparent to those skilled in the art and the generic principles herein may be applied to other embodiments. Thus, the present invention is not intended to be limited to the embodiment shown but is to be accorded the widest scope consistent with the principles and features described herein.

Figure 1:
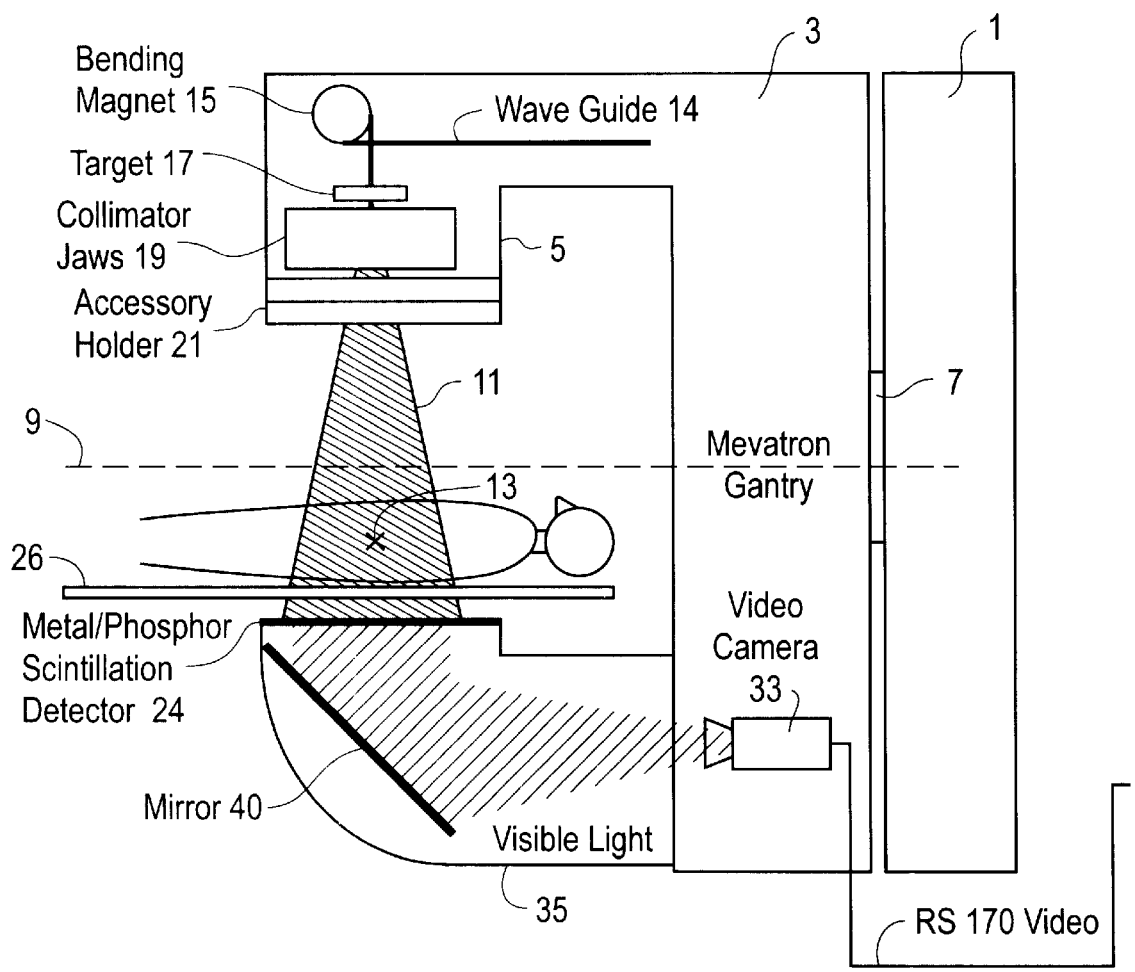
FIG. 1 is an illustration of a radiation emitting apparatus suitable for implementing an embodiment of the present invention.

FIG. 1 is a schematic diagram of an example of a linear accelerator treatment device suitable for implementing an embodiment of the present invention. FIG. 1 shows a linear accelerator device with a stand 1 which is typically anchored firmly to the floor. Stand 1 supports a gantry 3 including a treatment head 5. Gantry 3 can be rotated on bearing 7 around a horizontal axis 9. Gantry 3 and treatment head 5 include a waveguide 14 which accelerates electrons. Waveguide 14 is coupled with a bending magnet 15 which directs the electron beam through target 17 and into collimator 19. The resulting beam may also be radiated through some type of accessory in the accessory holder 21.

Stand 1 typically includes an electron injector which supplies injector pulses to an electron gun located in gantry 3. Electrons are emitted from the electron gun into waveguide 14 to be accelerated. An electromagnetic field supplied to waveguide 14 typically accelerates the electrons emitted by the electron gun for forming an electron beam. In treatment head 5, the electron beam typically enters an evacuated envelope which bends the electron beam, for example, by 270 degrees. The electron beam then exits the envelope through a window. If electron radiation is to be generated, a scattering foil is typically moved into the trajectory of the electron beam. If x-ray radiation is to be generated, a target is typically moved into the trajectory. The current of the electron beam is higher for X-ray radiation than for the generation of the electron radiation because more current is necessary to generate x-ray radiation due to deceleration of the electrons in the target. The x-rays are typically of penetrating power and may be used for the treatment of deep seated tumors, whereas the electrons themselves may be used directly to treat more superficial cancers. During treatment, the patient rests on a treatment couch 26 and intersects the treatment area at an isocenter 13.

A retractable and collapsible portal imaging detector housing 35 may be located at a front surface of the gantry 3 to allow radiation treatment to be performed simultaneously with visualization of the patient's anatomy within the x-ray radiation beam. After passing through the patient's body, the x-rays impinge upon image detector 24, are reflected off mirror 40, and captured by a video camera 33. The video camera may be coupled with an integrated treatment work station wherein the functions and control of the video camera may be controlled in the same system as the functions and control of gantry 3 adjustments. Alternatively, video camera 33 may be coupled with a first computer system which may be electronically accessible by a second computer system, wherein the second computer system controls the motions and adjustments of gantry 3. Yet another alternative is for video camera 33 to be coupled to a video camera computer system while the motions and control of gantry 3 are coupled to a separate computer system.

Figure 2:
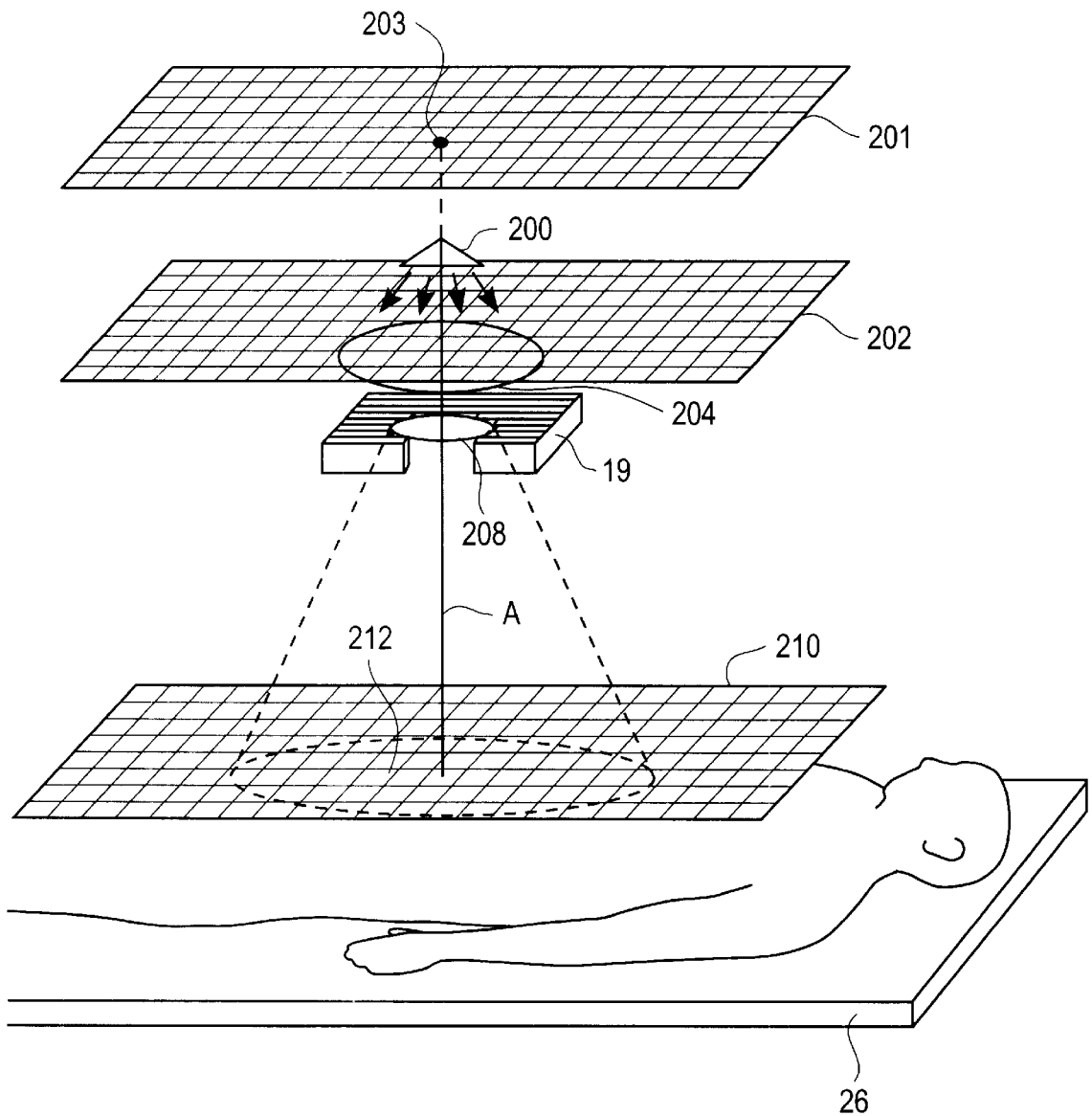
FIG. 2 is an illustration of the radiation beam flowing from a source plane and through a scattering plane and a calculation plane.

FIG. 2 is an illustration of a radiation beam flowing from a source plane 201 through the hypothetical constructs of a scattering plane 202 and a calculation plane 210. The source plane 201 is drawn at the location of the target 17. Point 203 on source plane 201 is the location where the beam strikes the target. The diagram of FIG. 2 shows a patient lying upon a patient table 26 with a radiation beam flowing through a flattening filter 200 located above the patient. The primary function of the flattening filter 200 is to encourage the radiation intensity to be uniform over the field. Once the radiation beam flows through the flattening filter 200, there are primary rays of the radiation beam, which flow radially down from the target and down to the patient. In addition to the primary rays, some rays are scattered in various directions. Some of these scattering rays will bounce off objects and eventually reach the patient. In determining the fluence over the patient, the contributions from both the primary rays and the scattering rays need to be considered.

Once the radiation beam flows through the flattening filter 200, the rays flow through a dose chamber 204. After the dose chamber, the radiation beam flows through a collimator aperture 208 defined by a collimator 19 and on to the patient. A hypothetical construct, herein referred to as a scattering plane 202, is situated between the flattening filter 200 and the dose chamber 204. The scattering plane 202 is typically divided into a plurality of squares. Each square in the scattering plane 202 may be considered a source of radiation. Each scatter source provides a scatter element $\Delta s$ defined as:

$$\Delta s \approx A e^{(-br)}$$

wherein:

s is the scatter element;

A is amplitude;

e is the exponential function;

b is an attenuation coefficient; and r is the radial distance from a central axis of the radiation beam.

Other functions may be suitable, and while the current embodiment uses the exponential function, the method is not limited to using the exponential function; a Gaussian or any other radially symmetric function that decreases with radial distance and which can fit the experimental data can be used. A central axis A is defined as a line flowing straight through the center of the flattening filter 200. According to this approximation, the scattering source intensity diminishes exponentially as the source location moves away from the central axis. For further information regarding modeling radiation beams using a scattering plane, one may refer to *Head Scatter Modeling for Irregular Field Shaping and Beam Intensity Modulation*, by Hounsell & Wilkinson, PHYS. MED. BIOL. 42 (1997) 1739–1747, IOP Publishing Ltd.

Another hypothetical construct, a calculation plane 210 (sometimes referred to as a patient plane, or an isocentric plane) may also be thought of as being positioned directly above the patient. The calculation plane 210 is also typically divided into squares. When a radiation beam, such as an x-ray beam, reaches a patient, it will cover an area 212 of the calculation plane 210. The area 212 covered by the radiation beam on the calculation plane 210 is the area that a fluence calculation is performed. Calculation points discussed herein refer to calculation points within the area 212 covered by the radiation beam. As previously mentioned, fluence describes the distribution of radiation intensity and is defined as the number of photons per area per time.

Figure 3A:
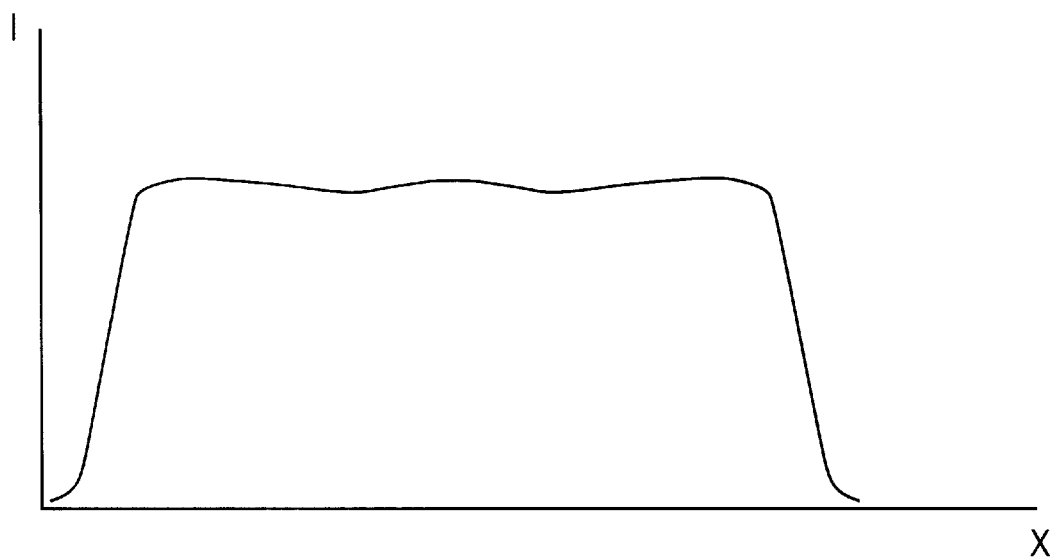
FIGS. 3A–3B show graphs of radiation intensity over the calculation plane.
Figure 3B:
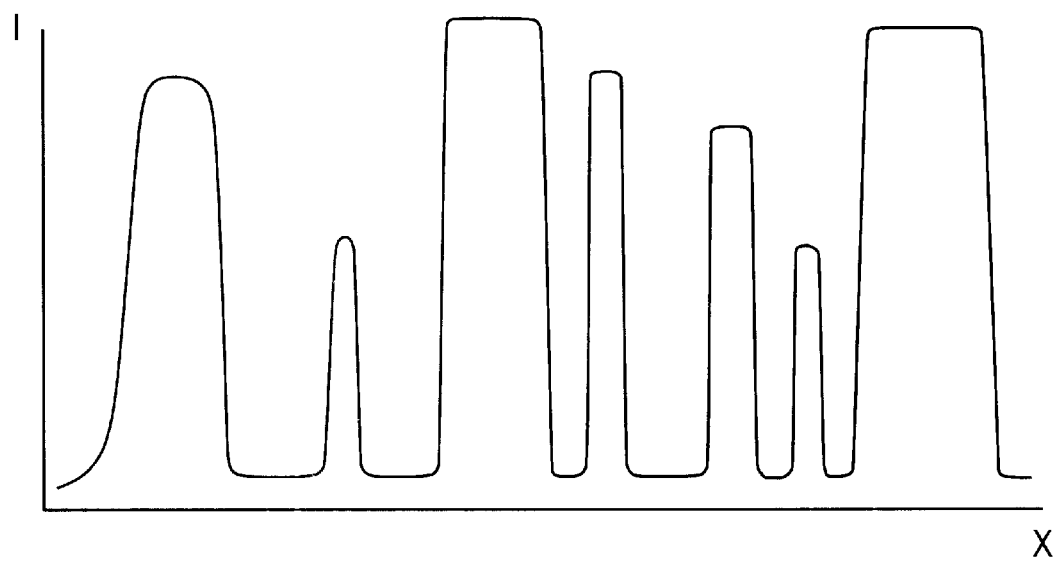

FIGS. 3A and 3B show graphs of radiation intensity over the calculation plane 210. Most conventional radiation treatments use a fairly steady radiation beam intensity, as shown in the graph of FIG. 3A. The radiation intensity over the affected area 212 of FIG. 2 may be approximately constant. However, in the field of intensity modulation, a superimposition of radiation fields may be used to maximize the radiation dose to a target, such as a tumor, and minimize the radiation dose to healthy tissue surrounding the target. The resulting graph of intensity over the area 212 is exemplified in FIG. 3B. The intensity of the radiation beam may vary dramatically throughout the affected area 212. Accordingly, an approximation of the fluence over one square of the calculation plane 210 would be entirely inaccurate for the remainder of the affected squares in the calculation plane 210.

Figure 4:
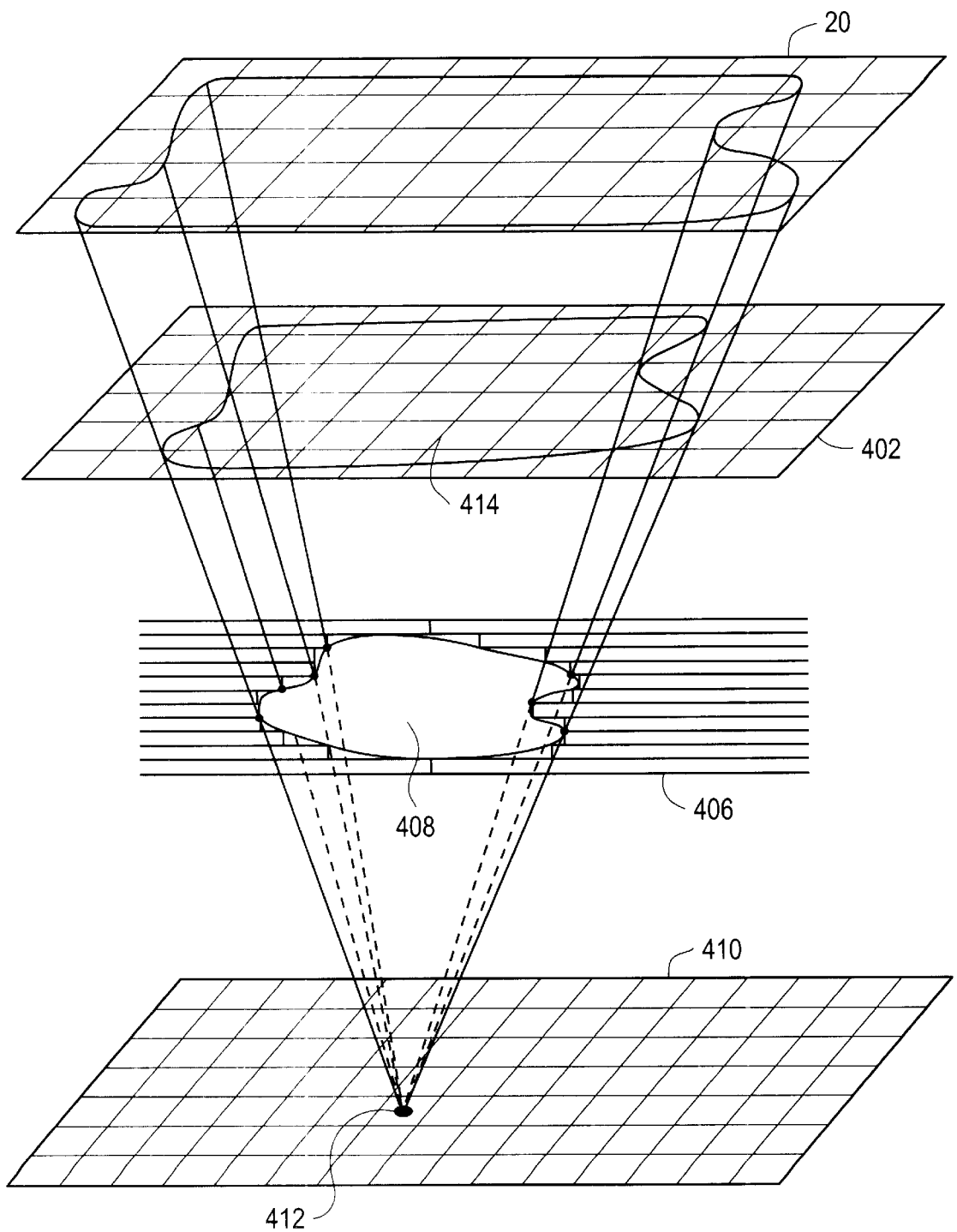
FIG. 4 is an illustration of an example of a method for calculating scatter radiation.

FIG. 4 illustrates an example of one method for calculating fluence over a calculation plane. FIG. 4 shows a collimator 406 positioned between a scattering plane 402 and a calculation plane 410. In this conventional method, a square on the calculation plane, herein referred to as a calculation point, may be analyzed by performing a ray tracing from the calculation point 412 to the collimator aperture 408. The aperture 408 may then be projected onto the scattering plane 402 such that projection 414 is defined on the scattering plane 402. This projection 414 should include all squares on the scattering plane 402 that may be a potential source of scattered radiation onto the calculation point 412.

In this method, the collimator 406 is treated as having an infinitesimal thickness. Assuming an infinitesimal thickness of a collimator 406 may cause inaccuracies in the scatter contribution of a calculation point. Additionally, this method may require a substantial amount of calculations. Thus, it would be desirable to have a method for calculating scatter radiation contribution to a calculation point which is fast and accurate. The present invention addresses such a need.

Figure 5:
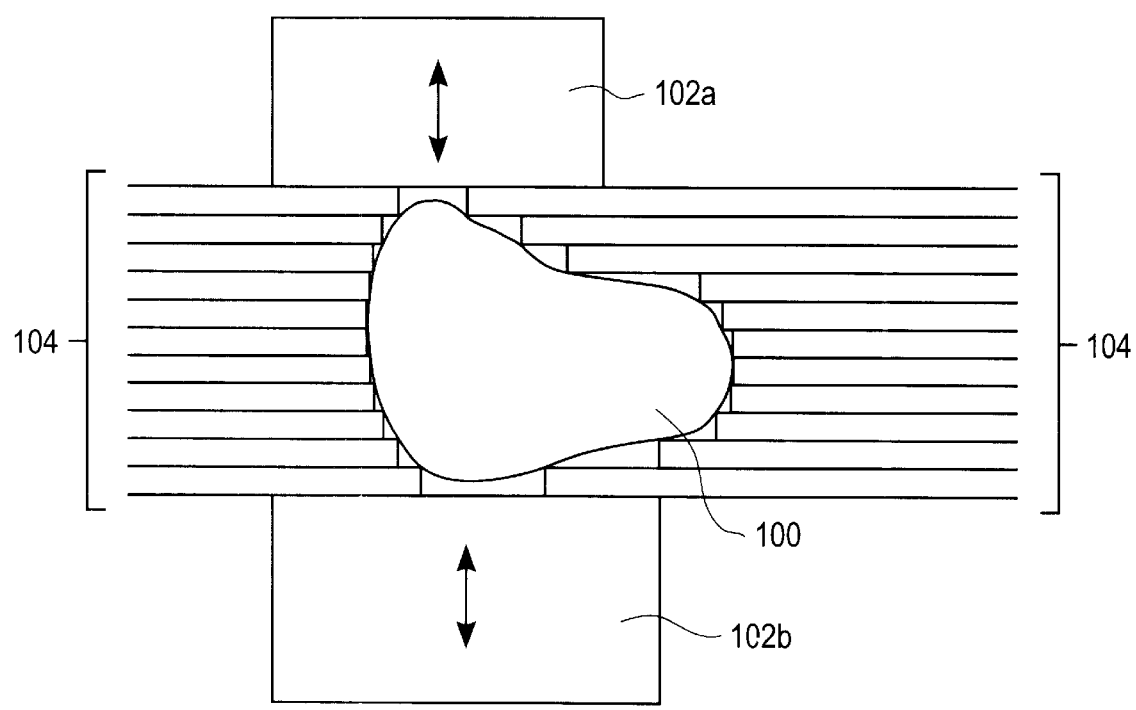
FIG. 5 is an illustration of a multi-leaf collimator suitable for use with an embodiment of the present invention.

FIG. 5 is an illustration of a multi-leaf collimator. In the example shown in FIG. 5, a multi-leaf collimator 19 is shown to be shaped around a target 100, such as a tumor. Tumor shapes are often irregular, and a multi-leaf collimator facilitates the application of minimal radiation to non-tumor tissues creating a treatment field closely approximating the shape of the tumor.

Multi-leaf collimator 19 includes leaves 104 located on opposite sides of target 100. Additionally, multi-leaf collimator 19 may also include a set of jaws 102a–102b located perpendicular to leaves 104. Jaws 102a–102b may be movable in a direction perpendicular to the longitudinal axis of leaves 104. Accordingly, jaws 102a–102b may approach each other to reduce the size of the x-ray field, or move away from each other to increase the size of the treatment field. Likewise, each leaf 104 may be moved along its longitudinal axis toward or away from an opposing leaf 104 to customize the field for a particular target 100, such as a tumor. The x-ray field is allowed to pass within the space between leaves 104 and jaws 102a–102b.

Figure 6A:
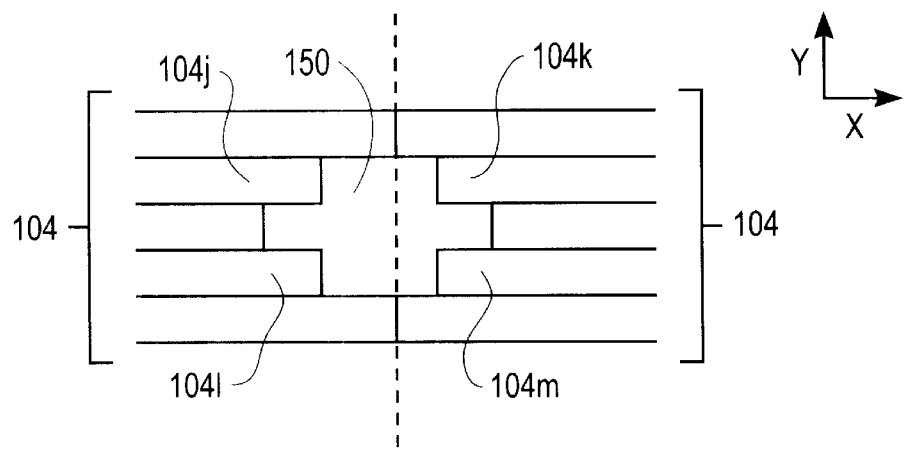
FIGS. 6A–6C show various perspectives of a collimator.
Figure 6B:
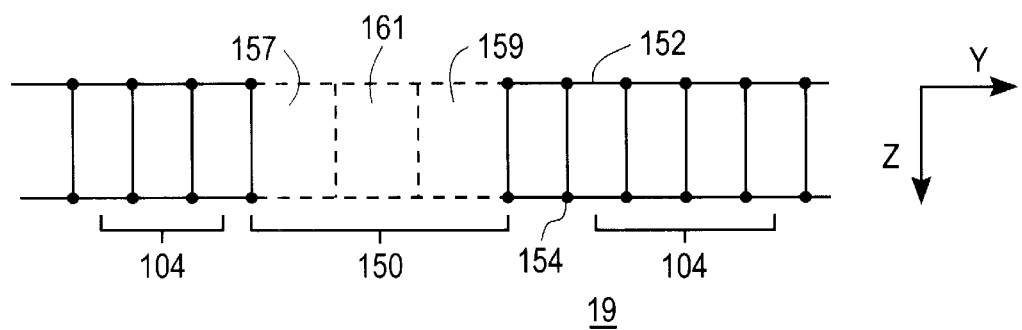
Figure 6C:
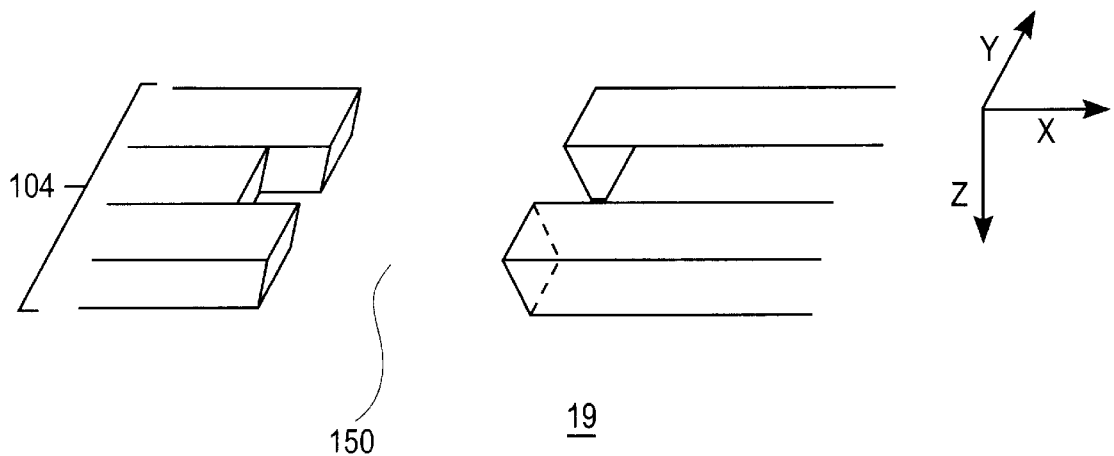
Figure 7:
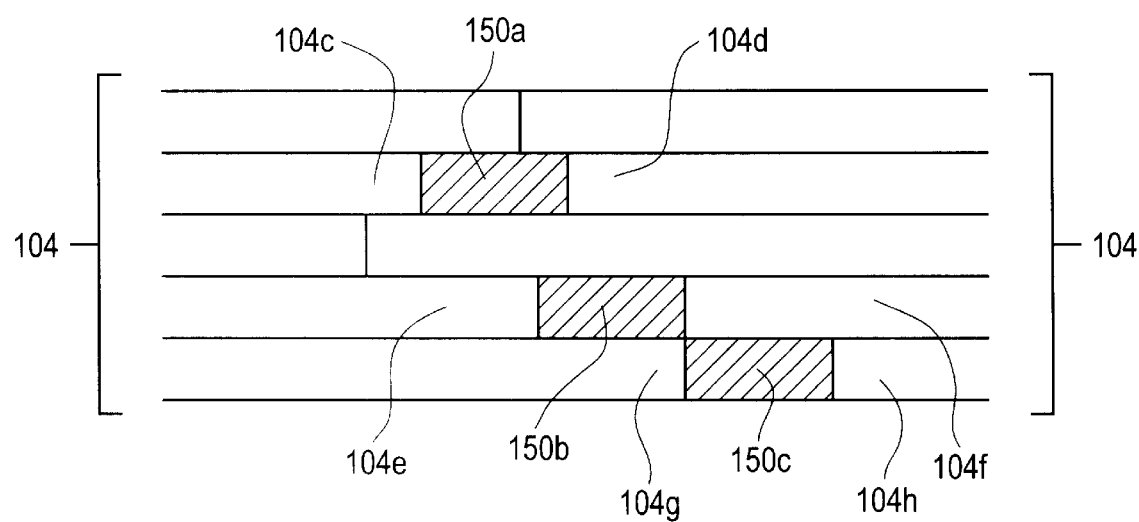
FIG. 7 illustrates multiple polygons which may be created by openings between leaves of a collimator.

FIGS. 6A–6C show illustrations of collimator 19 from various perspectives. For simplicity, the illustrations and calculations related to the collimator 19 shown in the remaining figures exclude jaws 102a–102b of FIG. 5, however, in the calculations, the jaws may be considered as an extra pair of leaves in collimator 19. FIG. 6A shows collimator 19 as seen in the x-y plane. In this figure, an aperture 150 is shown to be created by leaves 104. FIG. 6B shows collimator 19 in the y-z plane, while FIG. 6C shows leaves 104 of collimator 19 in perspective, indicating its three dimensional (x, y, z) nature. To simplify the fluence calculation, the calculation is performed in a series of two-dimensional calculations, according to an embodiment of the present invention, as described below with respect to the remaining figures. FIG. 7 is an illustration of collimator 19 with multiple apertures or polygons 150A–150C defined by leaves 104. Each polygon 150A–150C may be analyzed for scatter contributions.

Figure 8:
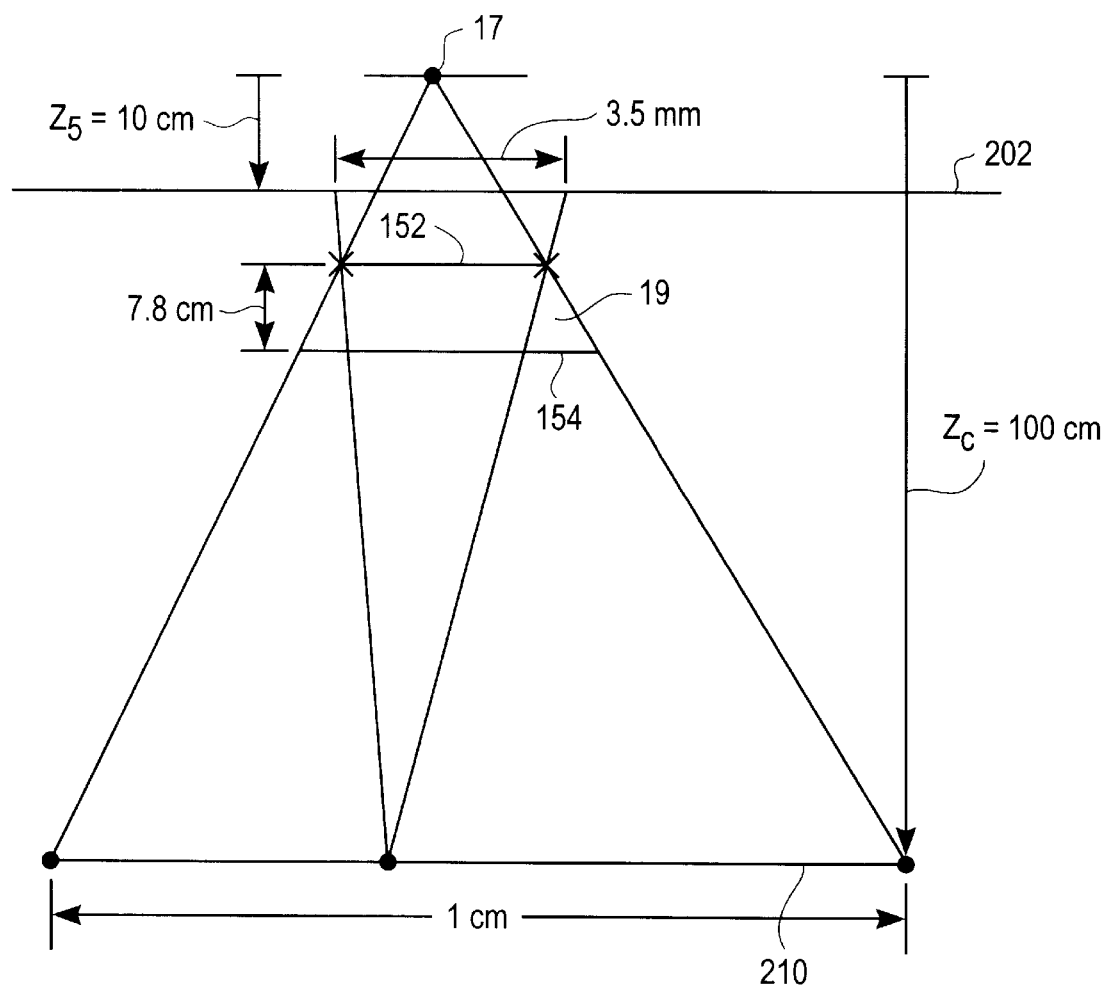
FIG. 8 is an illustration of scattering plane and calculation plane geometries according to an embodiment of the present invention.

FIG. 8 illustrates an example of comparative proportions for the scattering plane 202 and the calculation plane 210. In this example, scattering plane 202 is spaced approximately 10 cm from the source of the radiation beam, directly below flattening filter 200, and calculation plane 210 is located approximately 100 cm from the source of the radiation beam, target 17. The radiation beam flows through scattering plane 202 and collimator 19 and is projected onto calculation field 210. The collimator 19 may have a thickness of 7.8 cm, for example. The projection of the leaf width formed by the radiation beam as it travels from target 17 through collimator 19 and onto calculation plane 210 is approximately 1 cm. A projection of the collimator leaf top width from the calculation point onto the scattering plane 202 may be approximately 3.5 mm. Squares located on the scattering plane 202 may be approximately 1 mm×1 mm, while the rectangles in the calculation plane may be approximately 1 cm by an arbitrary amount, such as 1 cm. An example of the number of squares on calculation plane 210 is approximately 100 and the number of squares in scattering plane 202 could be as many as 10,000 squares.

The selection of a square in the scattering plane 202 is preferably such that the width of the scattering square is smaller than a scattering strip described below. The scattering squares should also be smaller than a square which is projected onto scattering plane 202 through collimator 19 from a point on calculating plane 210. Accordingly, an example of a size of a scattering square is 1 mm×1 mm. The following describes a method for defining scatter strips in the scattering plane 202 as disclosed in U.S. patent application Ser. No. 09/178,381 filed Oct. 23, 1998, which is incorporated herein by reference. The rays traced to the scattering plane 202 span an area (known as the scatter strip) that is generally too coarse for the calculation of source integrals in the source plane 210, however, the scatter strip can be treated as a rectangular area that can be projected onto the source plane to allow use of a finer grid on the source pane than the one used on the scattering plane with a minimum of repeated multiplication and addition operations. Since there is effectively no blocking elements from the scattering plane 202 to the source plane 201, the scatter strips defined on the scattering plane may be projected onto the source plane, and an integration of that part of the source plane inside the projected rectangular area can be performed using a rectangular integration method, as described below. The following describes first a process for defining the scatter strips on the scattering plane by ray tracing from the calculation plane. The ray tracing used to determine the left and right boundaries of each scatter strip in the scattering plane is used to continue the ray tracing onto the source plane, in order to determine the rectangular boundaries in the source plane that correspond to the scatter strip boundaries in the scattering plane. The rectangular areas projected on the source plane are then used to calculate fluence contributions with the use of a pre-integrated lookup table, as described below.

Figure 9:
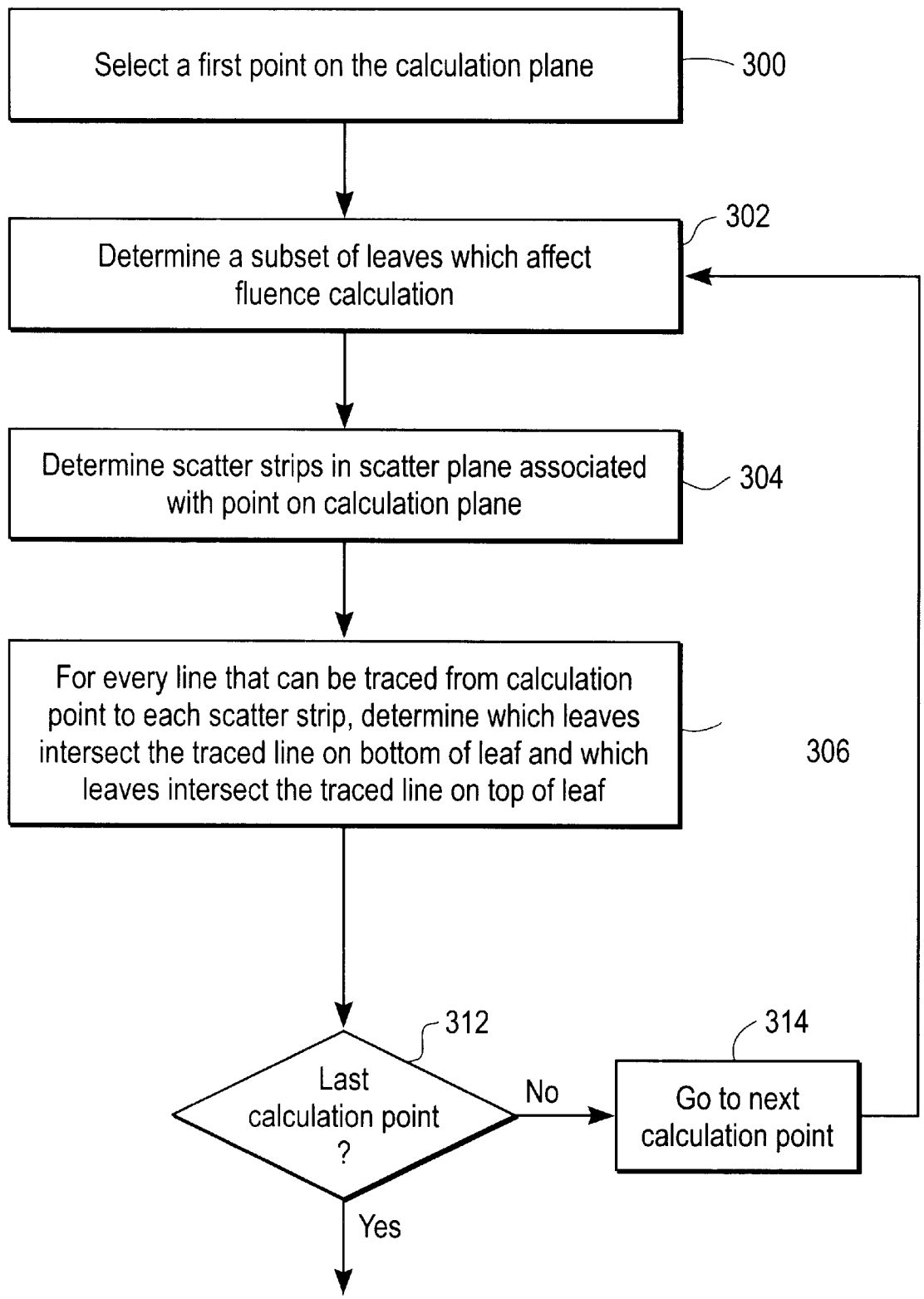
FIG. 9 is a flow diagram of a method for defining scatter strips of a scattering plane through ray tracing.

FIG. 9 is a flow diagram of a method according to an embodiment of the present invention for calculating scatter radiation. Initially, a first point on the calculation plane is selected (step 300). As previously mentioned, a point on the calculation plane refers to a segment of the calculation plane, such as a calculation square. Further details of the selection of a first point on the calculation plane will later be discussed in conjunction with FIG. 10A.

A subset of collimator leaves which may affect the fluence calculation is determined (step 302). Details of determining such a subset of collimator leaves is later discussed in conjunction with FIGS. 10A–13, 16–17b. Scatter strips in the scattering plane which are associated with the selected point on the calculation plane is then determined (step 304). A scatter strip may include a portion of a scatter square, a single scatter square, multiple scatter squares, or any combination thereof, of the scattering plane. For every line that can be traced from the selected calculation point to each scatter strip on the scattering plane, the leaves which intersect the traced line on the bottom of the leaf and the leaves which intersect the traced line on the top of the leaf are determined (step 306). Further details of this determination will later be discussed in conjunction with FIGS. 10A–13, 15, 17A–17B.

FIGS. 10A–19C are further flow diagrams of a method for defining scatter strips on the scattering plane. Initially, the number of polygons to be analyzed is determined (step 400). An example of polygons to be determined is shown in FIG. 7. In the example shown in FIG. 7, the collimator 19 is shown to be arranged to create polygons 150A–150C. Further details of the determination of the number of polygons to be analyzed will later be discussed in conjunction with FIG. 14.

One of the polygons is then selected (step 402). A y-value of a calculation point in the calculation plane is then selected (step 404). At this step, the y-z plane is referenced, accordingly, it is not yet necessary to know the x values. The analysis for this one y value may be applied to all calculation points that have this same y value, even if they have different x values. At this step, one may conceptualize a calculation line rather than a calculation point, with the line having the same y and z coordinates and the line extending over all values of x (perpendicular to the y-z plane).

A maximum collimator leaf and a minimum collimator leaf for the selected polygon are then determined (step 406). FIG. 6b shows an example of a maximum leaf 159 and a minimum leaf 157 in collimator 19. In this example, the maximum and minimum refers to the first and last leaves of the polygon, respectively. These maximum and minimum leaves 159 and 157 bracket the range of scatter strips that will be visible to a calculation point. The dashed lines represent all the leaves between and including the maximum and the minimum leaf. In determining the maximum and minimum leaves, all the leaves that are open in the polygon should be considered, not just those visible in a y-z perspective. A range of leaves between the minimum and maximum leaves of the polygon is then determined (step 408). In the example shown in FIG. 6B, the range of leaves between the minimum and maximum leaves includes leaf 161.

Figure 13:
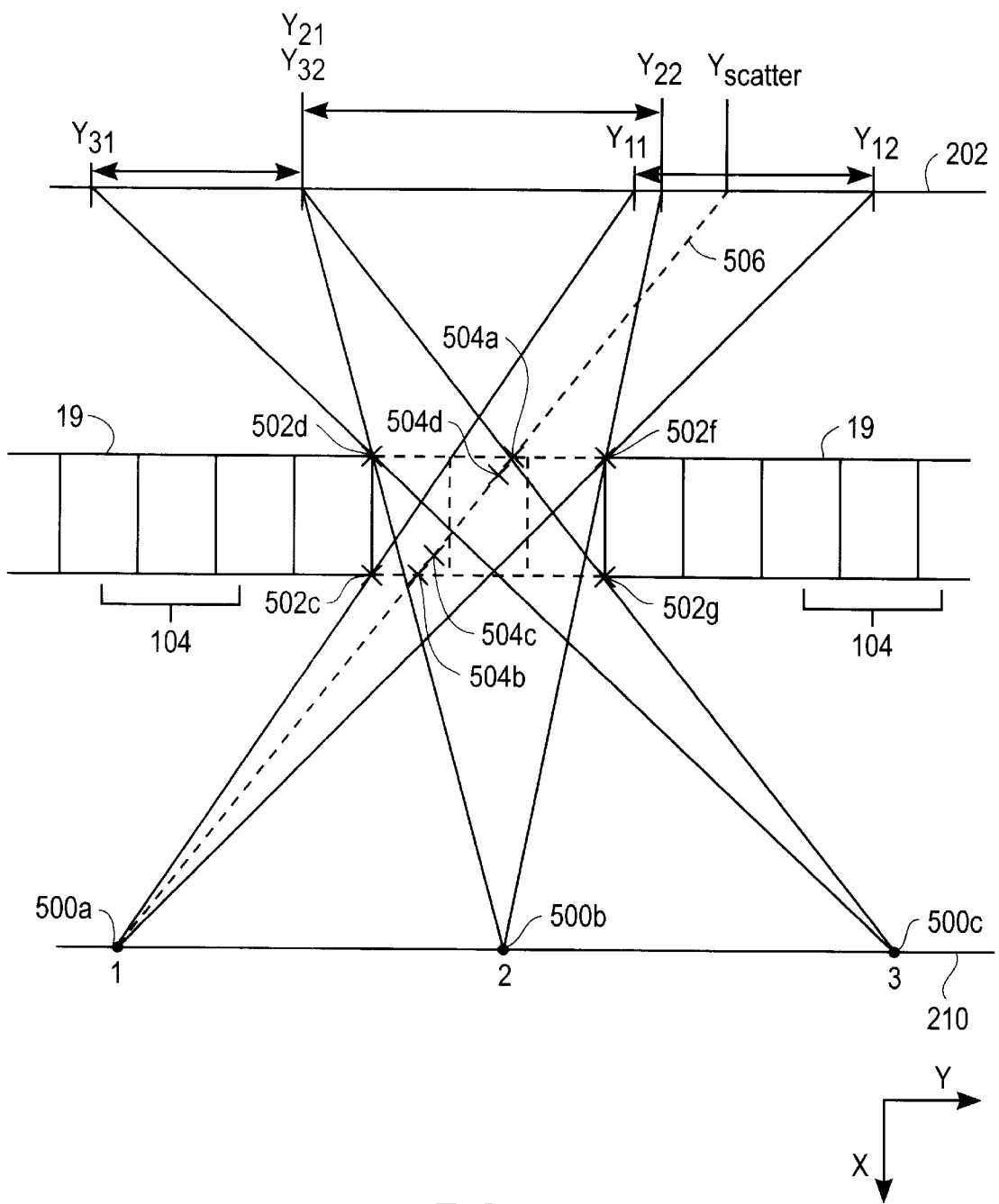

Collimator leaf points to be intersected by line traces from the selected calculation point to the scattering plane are established (step 410). At this point, all the calculations are performed for the y-z plane only. A line is traced from the line $y=y_c$, $z=100$ to the line $y=y_s$, $z=10$, assuming the values shown in the example of FIG. 8. Consider a perpendicular line from the line in the calculation plane that has one y value but several x values associated with it to the line in the scattering plane that has one y value but several x values associated with it also. In the y-z plane view, the x dimension has been collapsed into a single value, so that all x values are treated the same way in this plane. An example of collimator leaf points to be intersected by line traces from the calculation point to the scattering plane are shown in FIG. 13 (504a–d).

A minimum y and a maximum y of the scattering plane are then determined (step 412). The minimum and maximum y-values are the y-values of a projection from the calculation point to the scattering plane. For example, FIG. 13 is yet another diagram showing the collimator 19 located between calculation plane 210 and scattering plane 202. This perspective is shown in the y-z plane. As shown in this example, each calculation point 500A–500C on the calculation plane 210 is shown to have a projection onto the scattering plane 202. Each projection has a minimum y and a maximum y of the scattering plane 202. In this example, the minimum y associated with calculation point 500A is $y_{11}$, while the maximum y is $y_{12}$. Likewise, the minimum y and maximum y-values associated with calculation point 500B is $y_{21}$ and $y_{22}$; and the minimum and maximum y-value associated with calculation point 500C is $y_{31}$ and $y_{32}$.

For every line that can be traced from the calculation point on the calculation plane to each scatter strip within $y_1$ and $y_2$ ($y_s$), a point at leaf bottom level and a point at leaf top level are determined which intersects the traced line (step 414). The example shown in FIG. 13 shows a traced line 506 which is traced from the calculation point 500A to a scatter strip at $y_s$ of the scattering plane 202. The traced line 506 intersects a leaf bottom 504B and a leaf top level 504A.

Figure 10A:
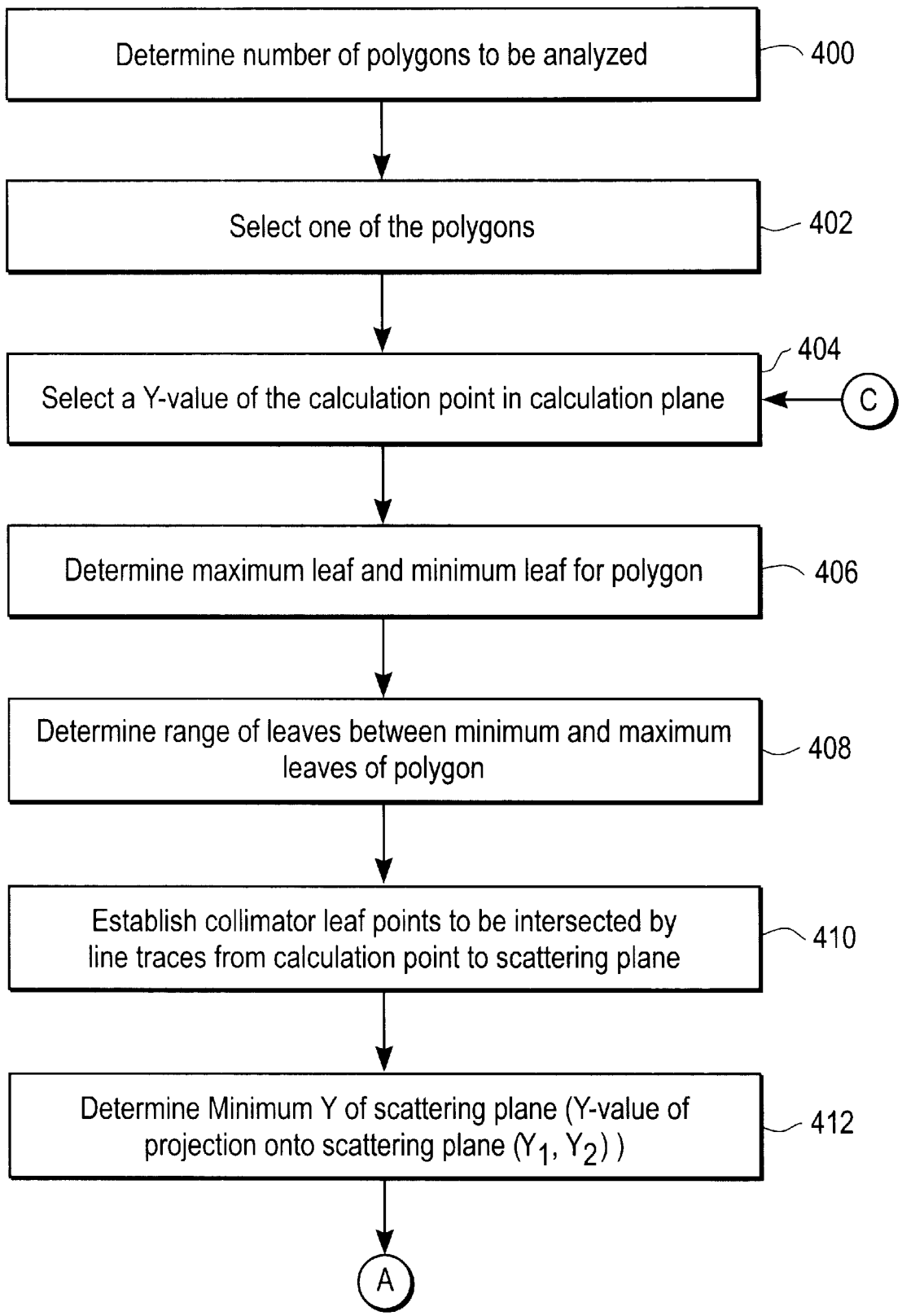
FIGS. 10A–10C are additional flow diagrams of a method for defining the scatter strips.
Figure 10B:
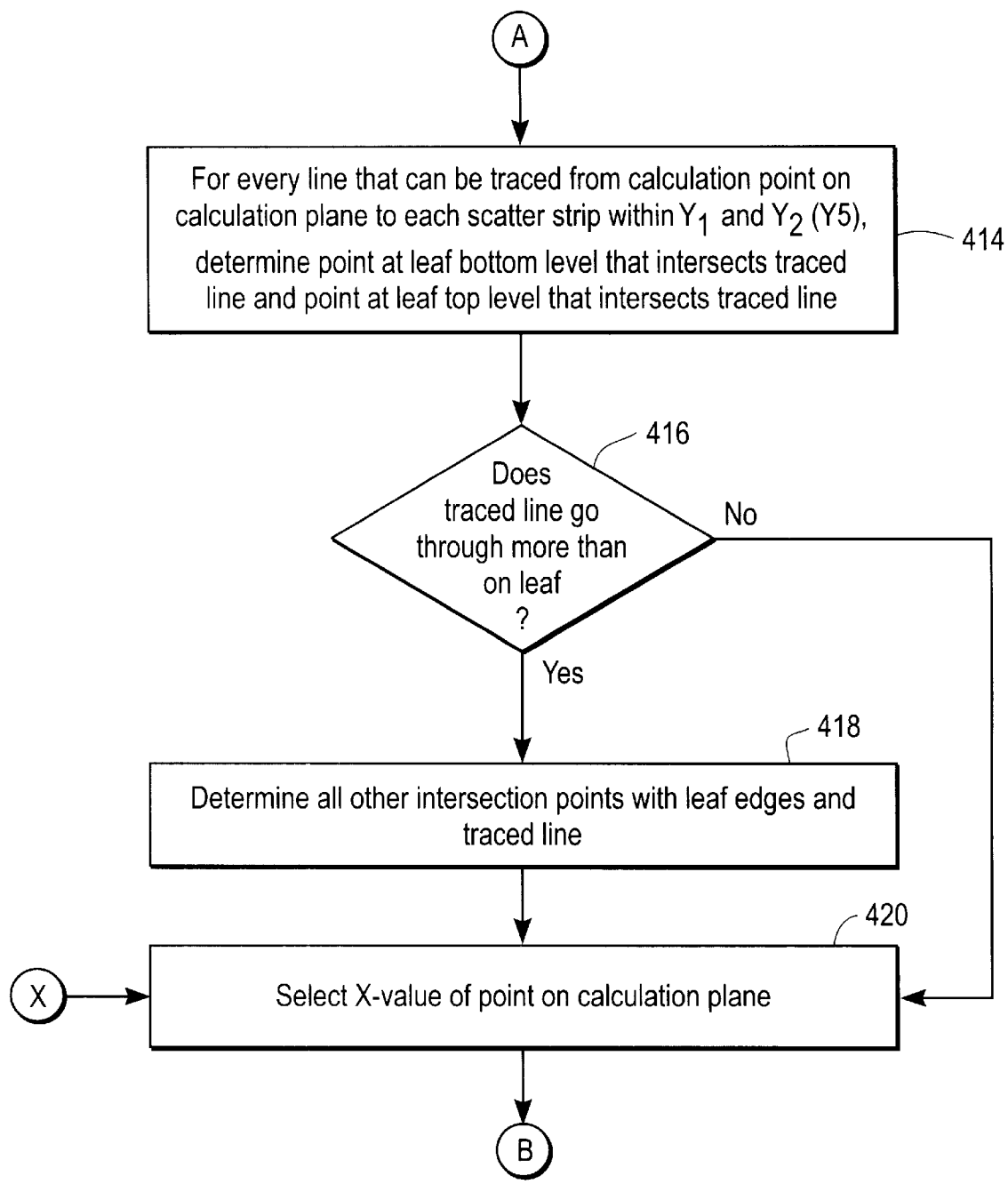

It is then determined whether the traced line traverses through more than one leaf (step 416 of FIG. 10B). Note that an intersection between a line and a leaf indicates a two-dimensional intersection, not a three-dimensional intersection. In three-dimensions, a ray does not necessarily intersect a given leaf, however, in a two dimensional collapsed view, such as the y-z plane view shown in FIG. 13, the ray appears to intersect the leaf.

In the example shown in FIG. 13, the traced line 506 does traverse through more than one leaf. When the trace line moves through more than one leaf, all of other intersection points with the leaf edges and the traced line are determined (step 418). In the example shown in FIG. 13, intersection points 504C and 504D are determined. Thereafter, an x-value of the point on the calculation plane is selected (step 420). If the traced line does not go through more than one leaf (step 416), then an x-value of calculation point on the calculation plane is selected (step 420).

Figure 10C:
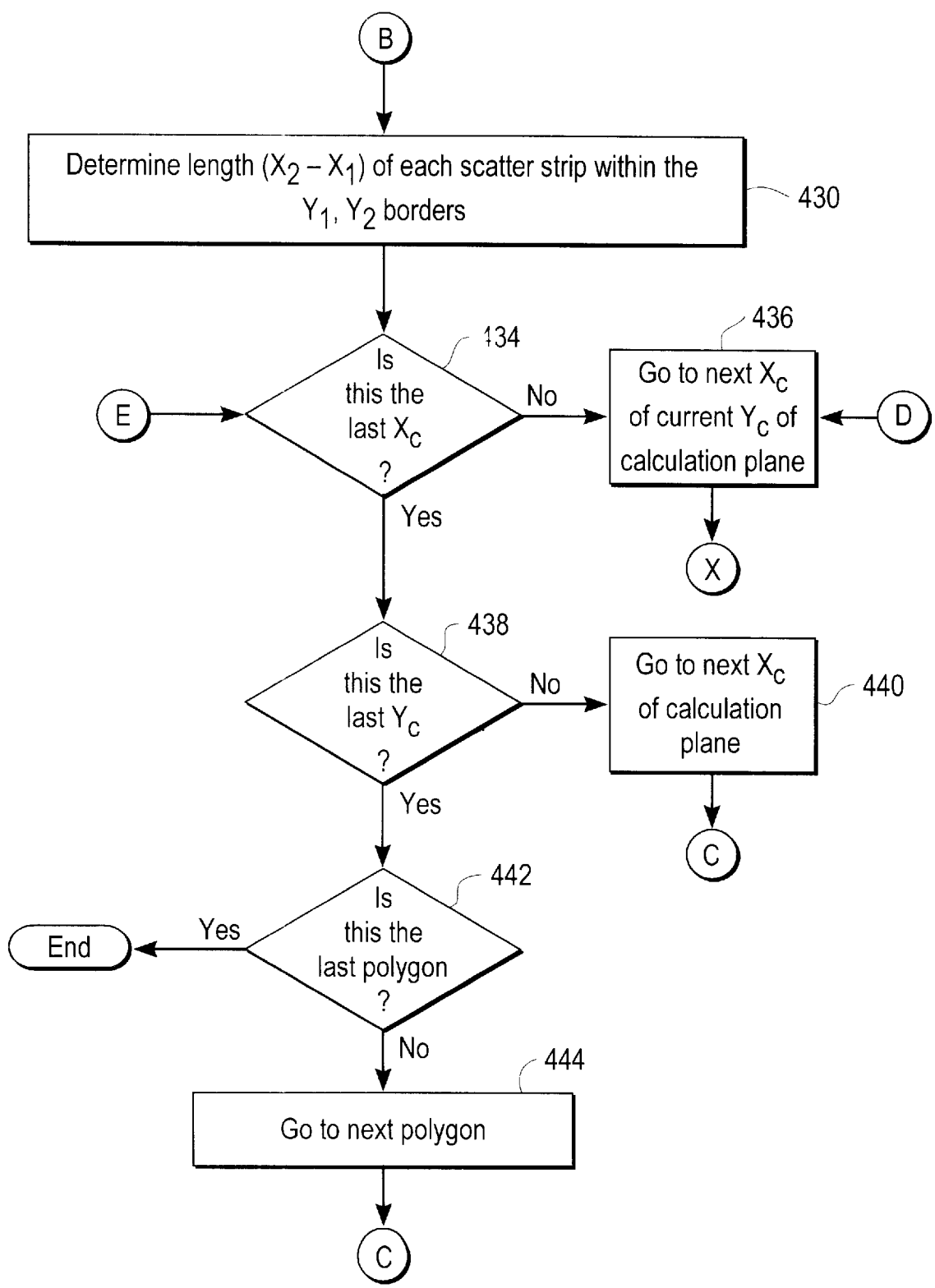

The length $(x_2-x_1)$ of each scatter strip ($y_s$) within the $y_1$, $y_2$ borders is determined (step 430 of FIG. 10C). In the example shown in FIG. 13, the perspective is shown in the y-z plane. Accordingly, only $y_S$ can be seen on the scattering plane 202. In this example, all scattering strips are perpendicular to the y-z plane, so only the intersection of each of these strips with the y-z plane is visible. However, in the perspective shown in FIG. 11, a similar diagram is shown in the x-y plane. In the x-y plane, the scattering plane 202 shows that a scattering strip 520 is shown to be located on the scattering plane 202. The scattering strip 520 has a length of $x_2-x_1$ at $y_S$. The scattering strip 520 is the scattering strip associated with the calculation point 500b.

It is then determined whether the x-value of the calculation point ($x_c$) is the last $x_c$ (step 434). If this is not the last $x_c$, then the next $x_c$ of the current y of the calculation plane ($y_c$) is analyzed (step 436 of FIG. 10C). Thereafter, a new x value of a point on the calculation plane is selected (420 of FIG. 10B).

If the current $x_c$ is not the last $x_c$, then it is determined whether the current y of the calculation plane ($y_c$) is the last $y_c$ (step 438). If the current $y_c$ is not the last $y_c$, then the next $y_c$ of the calculation plane is analyzed (step 440). Accordingly, a y-value of the new calculation point in the calculation plane is then selected (step 404 of FIG. 10A).

If this $y_c$ is the last $y_c$, then it is determined whether this polygon is the last polygon shaped by the collimator (step 442). If this is the last polygon, then the fluence calculation is complete. If, however, this is not the last polygon, then the next polygon is analyzed (step 444). Accordingly, a new y-value of the new calculation point in the calculation plane is selected to analyze the new polygon (step 404 of FIG. 10A).

Figure 14:
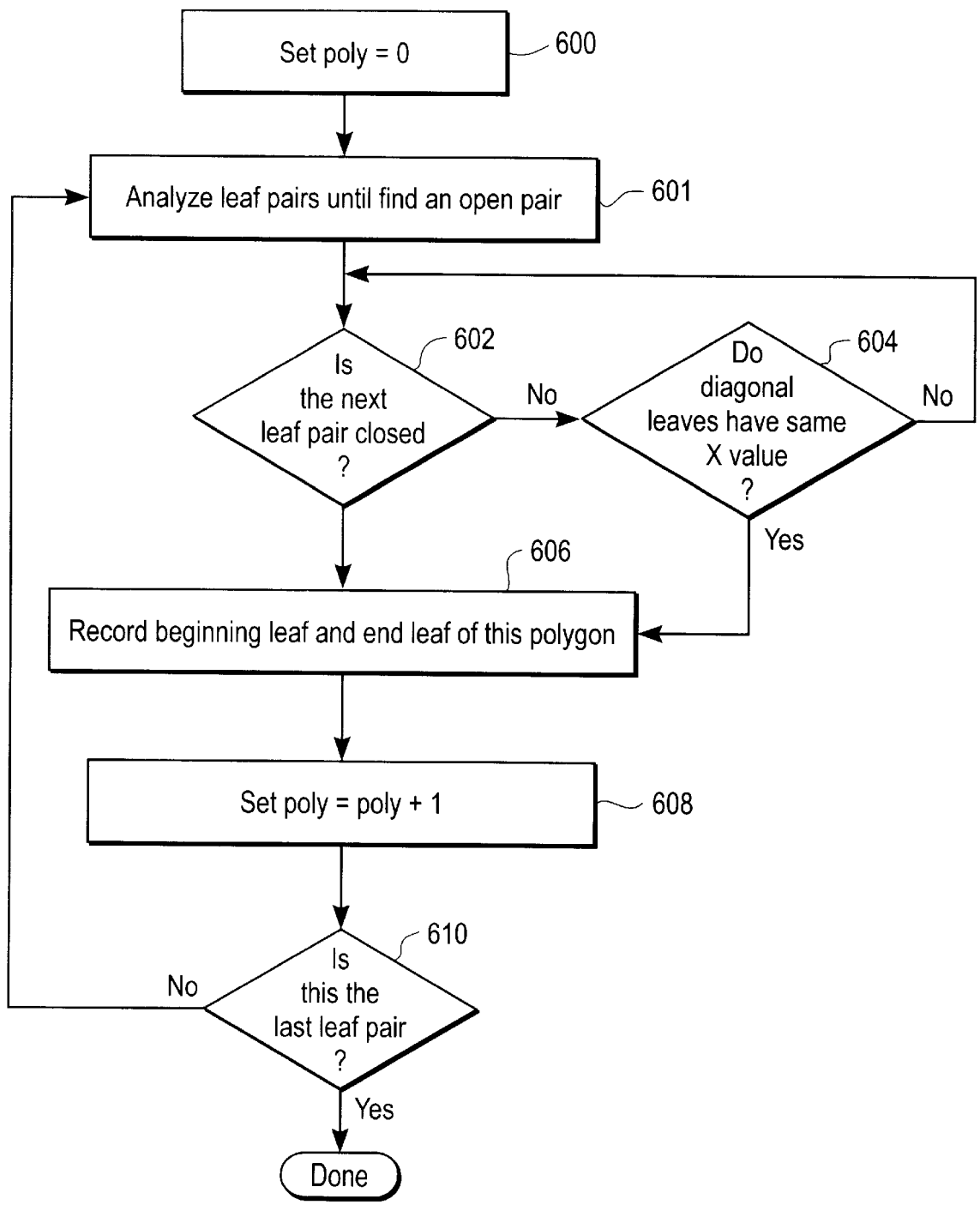
FIG. 14 is a flow diagram of a method for determining the number of polygons in a collimator.

FIG. 14 is a flow diagram of a method according to an embodiment of the present invention for determining the number of polygons, such as the determination of step 400 of FIG. 10A. A variable, "poly", is initially set to 0 (step 600), and all collimator leaf pairs are analyzed until a first open pair of collimator leaves is found (step 601). It is then determined whether the next leaf pair analyzed after the first open pair is closed (step 602). If the next leaf pair is not closed, then it is determined whether diagonal leaves have the same x-value (step 604). For example, in FIG. 7, the leaf pair 104C and 104D is open, while the next leaf pair is closed. Also, the leaf pair including leaves 104E and 104F is open and diagonal leaves 104F and 104G have the same x-value since their adjacent corners are aligned.

If the diagonal leaves do not have the same x-value (step 604), then the next leaf pair is analyzed to determined if it is closed (step 602). If, however, diagonal leaves do have the same x-value (step 604), or the next leaf pair is closed (step 602), then the beginning leaf pair and the end leaf pair of this polygon are recorded (step 606). In the example shown in FIG. 6A, the beginning leaf pair 104J and 104K would be recorded, and the end leaf pair 104L and 104M of polygon 150 would be recorded. In this example, the beginning leaf pair 104J and 104K is the first pair that is open, and the end leaf pair 104L and 104M is the last pair that is open.

Thereafter, the next polygon is analyzed ("poly" is set=to "poly"+1) (step 608). It is then determined whether this leaf pair is the last leaf pair (step 610). If this leaf pair is not the last leaf pair, then the process starts over in step 601 to find the very next open pair. If, however, this leaf pair is the last leaf pair, then the number of polygons has been determined.

Figure 15:
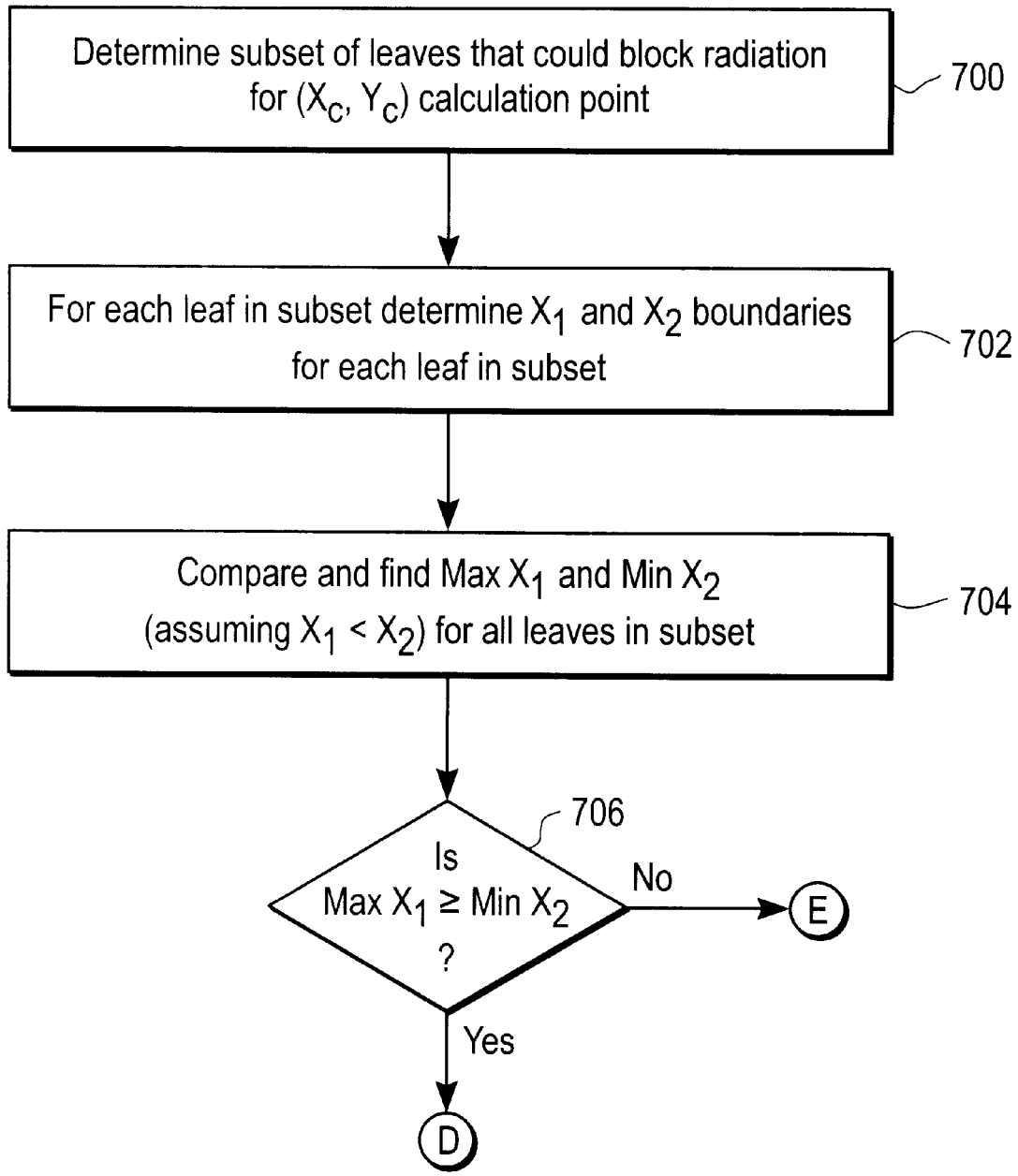
FIG. 15 is a flow diagram of a method for determining a length of each scatter strip.

FIG. 15 is a flow diagram of a method for determining a length ($x_2-x_1$) of each scatter strip, such as the determination made in step 430 of FIG. 10C. With regard to the hypothetical construct of the scattering plane, the scatter strip may include a portion of a scatter square, a single scatter square, multiple scatter squares, or any combination thereof.

A subset of collimator leaves that could block radiation for an analyzed calculation point ($x_c$, $y_c$) is determined (step 700). Further details of determining the subset of leaves is later discussed in conjunction with FIG. 16. For each leaf in the subset, an $x_1$ and $x_2$ boundary for each collimator leaf in the subset is determined (step 702). $X_1$ is a projection of a ray from the calculation point on the calculation plane to the scattering plane traversing across a leaf on side A of the collimator (see FIG. 11), while $x_2$ is a projection of a ray from the calculation point to the scattering plane traversing across a leaf on side B of the collimator. Details of such determination is later discussed in conjunction with FIGS. 17A and 17B. All of the $x_1$ and $x_2$ for all of the collimator leaves in the subset are compared and a maximum $x_1$ and a minimum $x_2$ (assuming $x_1$ is less than $x_2$) are found for all leaves in the subset (step 704). Details of finding the maximum $x_1$ and the minimum $x_2$ is later discussed in conjunction with FIGS. 17A and 17B.

It is then determined whether the maximum $x_1$ is greater or equal to the minimum $x_2$ (step 706). The $x_1$ and $x_2$ of each leaf in the subset is an indication of how far each leaf is out into the radiation field. The maximum $x_1$ and the minimum $x_2$ are usually, but not always, associated with the leaves which are the furthest out into the radiation field from each side of the collimator leaves. For example, in the diagram shown in FIG. 11, leaves 104A and 104B are the leaves associated with the maximum $x_1$ and the minimum $x_2$, respectively, for calculation point 500b, and they also happen to be the furthest leaves out into the radiation field for sides A and B of the collimator leaves.

The maximum $x_1$ and the minimum $x_2$ are actually associated with the leaves that block out the most radiation, and this is not necessarily the leaves that are furthest out into the field. While that is the case for a calculation point that is not behind any leaf bank (that is $x_c$>XAMAX and $x_c$<XBMIN, as is the case with point 500b of FIG. 11), for points such as 500a and 500c that are behind leaf banks, the maximum $x_1$ and the minimum $x_2$ may be associated with leaves other than the furthest out in the radiation field. For example, if leaf 104c in FIG. 11 had its edge 580 just slightly to the left of edge 582 of leaf 104a, then edge 580 would intersect the ray trace going from 500a to point 572, rather than edge 582. In that situation, leaf 104c would block more radiation despite it not being the furthest out in the radiation field. If maximum $x_1$ is greater or equal to the minimum $x_2$, then no radiation will be received at that calculation point. Accordingly the next point on the calculation plane is analyzed via step 436 of FIG. 10C.

Figure 16:
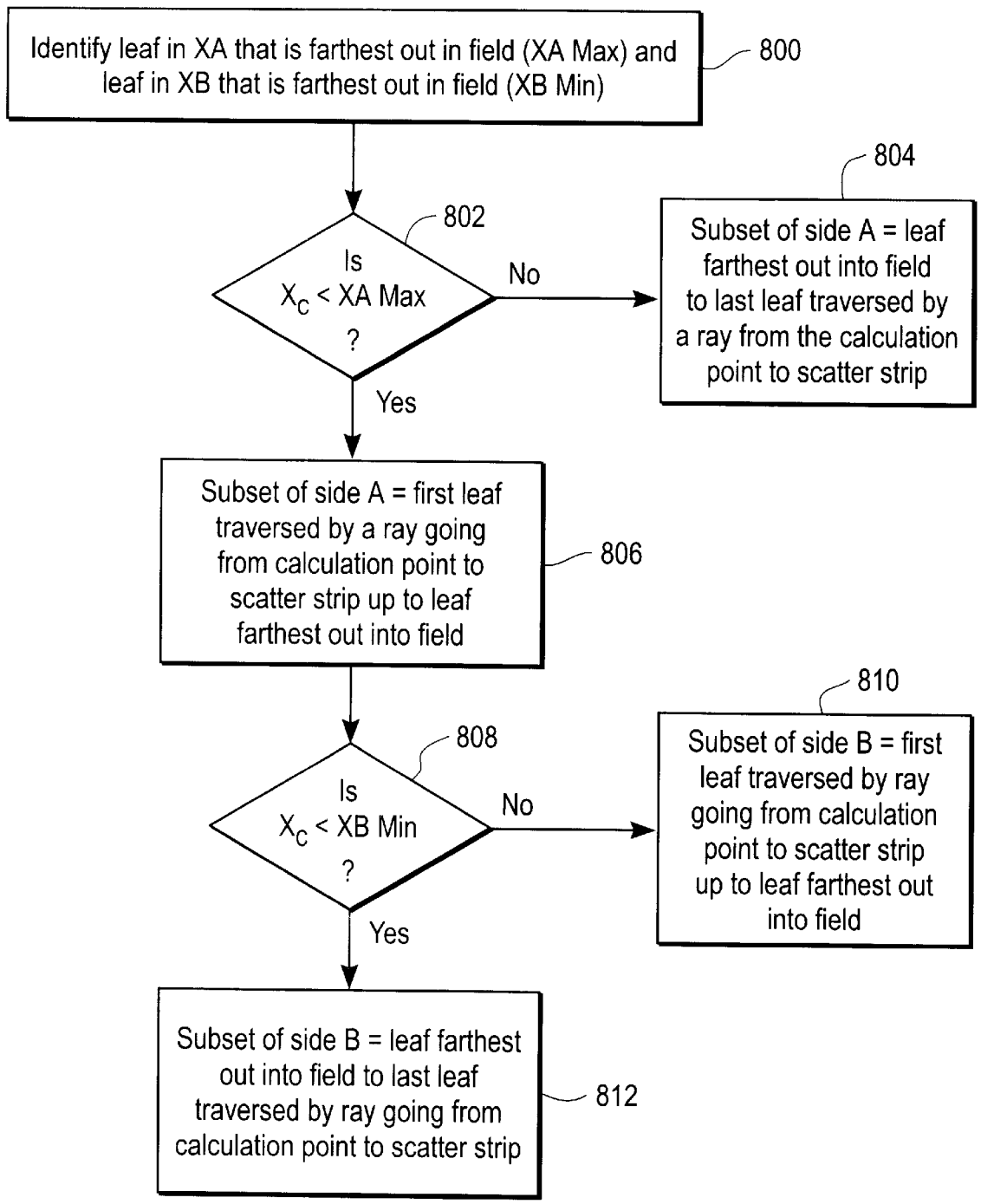
FIG. 16 is a flow diagram of a method for determining a subset of collimator leaves.

FIG. 16 is a flow diagram of a method for determining a subset of leaves that could block radiation for a particular calculation point ($x_c$, $y_c$), such as the determination made in step 700 of FIG. 15. Initially, a leaf that is the furthest out in the radiation field on either side of the collimator is identified (step 800). In the example shown in FIG. 11, the collimator 19 has leaves on side "A" and on side "B". In the example shown in FIG. 11, the leaf furthest out in the radiation field on the "A" side is shown to be leaf 104A. The leaf which is furthest out into the field on the "B" side is shown to be leaf 104B. These leaves have been designated as XAMAX and XBMIN, respectively.

It is then determined whether $x_c$ of the current calculation point is less than XAMAX (step 802). In the example shown in FIG. 11, calculation point 500A is located in a position such that the $x_c$ of the calculation point 500A is less than the x associated with leaf 104A which is the furthest out into the radiation field on side "A" (XAMAX). Calculation points 500B and 500C are shown to have an $x_c$ which is greater than or equal to XAMAX. Note that XAMAX is an x value associated with the position of the leaf furthest out into the radiation field on side A of the collimator, such as leaf 104a of FIG. 11, wherein the x value is a projection down to the calculation plane from the target. FIG. 8 shows an example of a projection down to the calculation plane 210 from the target 17.

If $x_c$ is not less than XAMAX, then the subset of leaves of side "A" is the set of leaves from the leaf furthest out into the field to the last leaf traversed by a ray from the calculation point to the scatter strip (step 804). In the example shown in FIG. 11, the subset is subset 560. If, however, $x_c$ is less than XAMAX, then the subset of leaves of side "A" is defined by the first leaf traversed by a ray going from the calculation point to the scatter strip up to the leaf that is the furthest out into the field (step 806). In the example shown in FIG. 11, this subset would be subset 562.

It is then determined whether $x_c$ is less than XBMIN (step 808). The XBMIN value is also an x value projected onto the calculation plane from the target. The XBMIN value is associated with the position of the leaf furthest out into the radiation field on side B of the collimator, such as leaf 104b of FIG. 11. In the example shown in FIG. 11, calculation points 500A and 500B are shown to have an $x_c$ less than XBMIN, while calculation point 500C is shown to have an $x_c$ greater or equal to XBMIN. If the $x_c$ of the calculation point is greater or equal to XBMIN, then the subset of leaves for side "B" is defined by the first leaf traversed by a ray going from the calculation point to the scatter strip up to the leaf furthest out into the field (step 810). In the example shown in FIG. 11, this subset only includes leaf 104B.

If the $x_c$ of the calculation point is less than XBMI, then the subset of leaves of side "B" is defined by the leaf furthest out into the field to the last leaf traversed by a ray going from the calculation point to the scatter strip (step 812). In the example shown in FIG. 11, this subset includes all of the leaves shown inside "B".

Figure 17A:
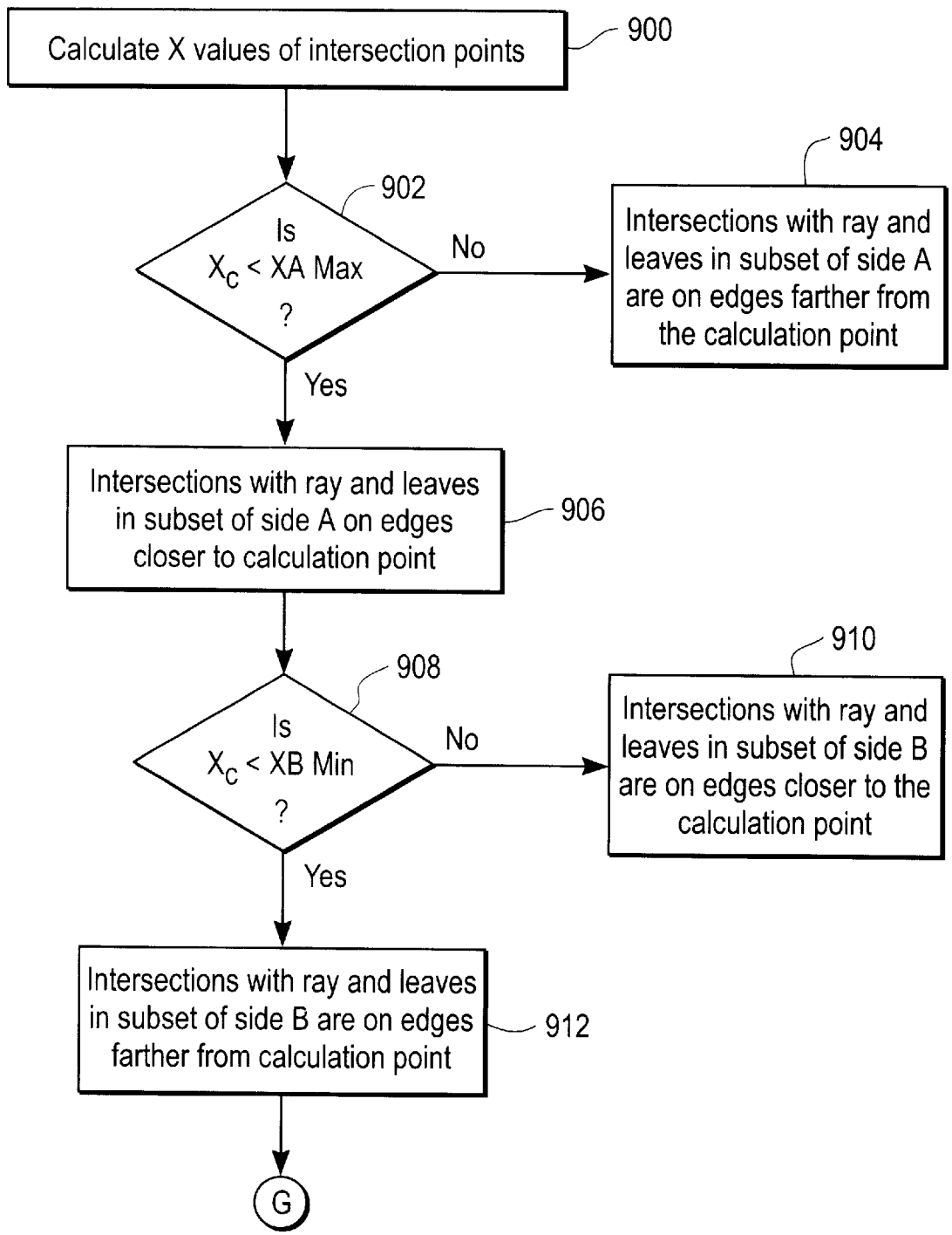
FIGS. 17A–17B are flow diagrams of a method for determining minimum and maximum boundaries for all scatter strips of all leaves in the subset of leaves.
Figure 17B:
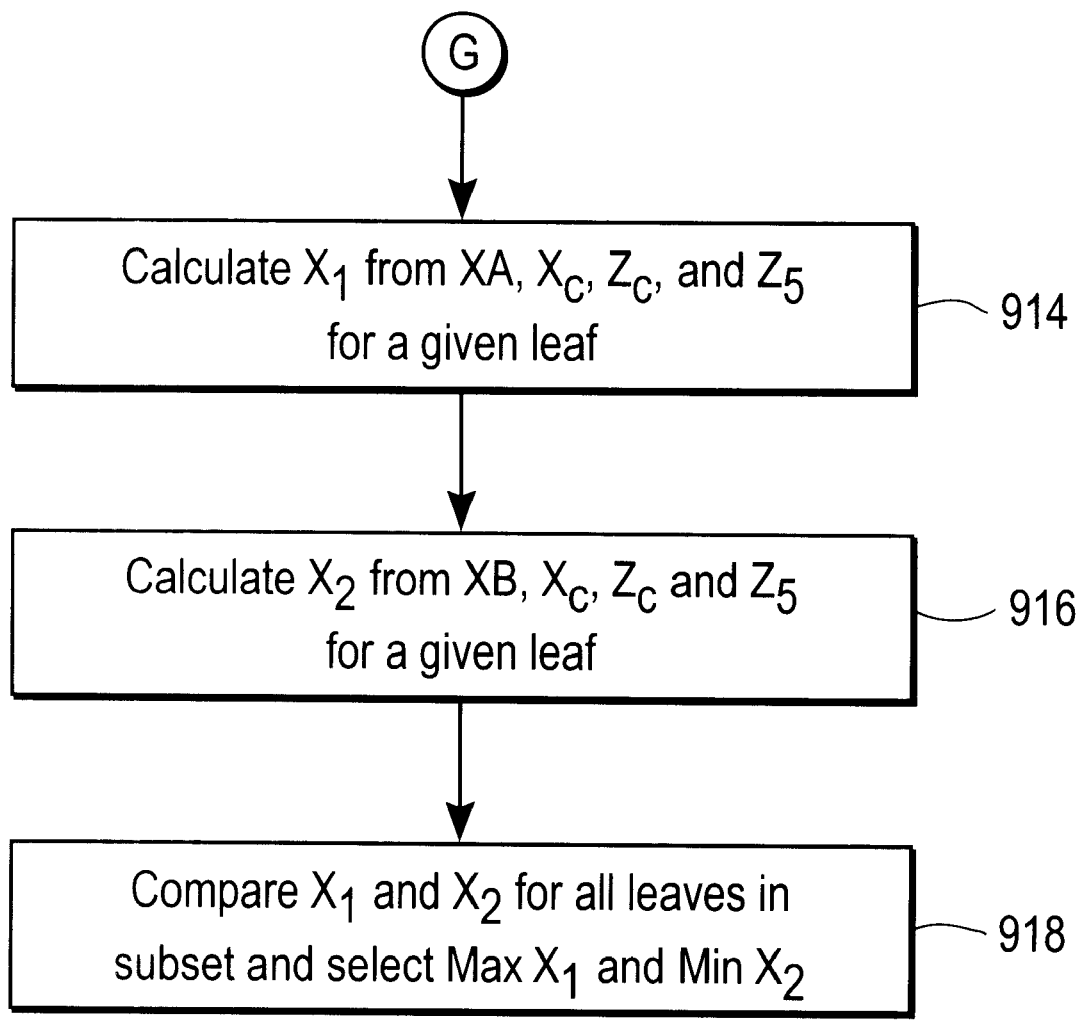

FIG. 17A is a flow diagram of a method according to an embodiment of the present invention for determining the boundaries ($x_1$ and $x_2$) for each collimator leaf in the selected subset and for determining the maximum $x_1$ and the minimum $x_2$ of all the leaves of the subset, such as the determinations of sets 702 and 704 of FIG. 15. The x-values of intersection points are calculated (step 900). Earlier, in steps 414 and 418 of FIG. 10B, and also in the discussion regarding FIG. 13, the y and z values of each intersection point had been determined. Accordingly, an equation may be solved for each leaf to determine the x-values of the intersection points in light of the previously determined y and z values.

For a given leaf and a given z value corresponding to an intersection point with that leaf, the x-value for that intersection point can be determined from the initial specification of the position of that leaf. The initial specification of the position of the leaves should be one of the inputs to the process (as for example, in FIG. 5, the aperture 100 is defined in terms of the leaf positions of the leaves 104). These specified leaf positions are the positions of the edges of shadows cast by the leaves onto the calculation plane from a point source at the target position (such as source 17 of FIG. 8) (These are the projected leaf positions, call the variable $x_p$). Because the edges of the collimator are divergent, the ratio of the x value of the intersection point to $x_p$ is equal to the ratio of the z value of the intersection point to the z value of the calculation plane ($z_c$). Hence:

$$x_i = x_p(z_i/z_c).$$

where $z_i$ is the z value of the intersection point, $z_c$ is 100 cm in the example shown in FIG. 8, $x_i$ is the x value of the intersection point, and $x_p$ is the projected leaf position of the leaf that contains the intersection point being evaluated.

Figure 11:
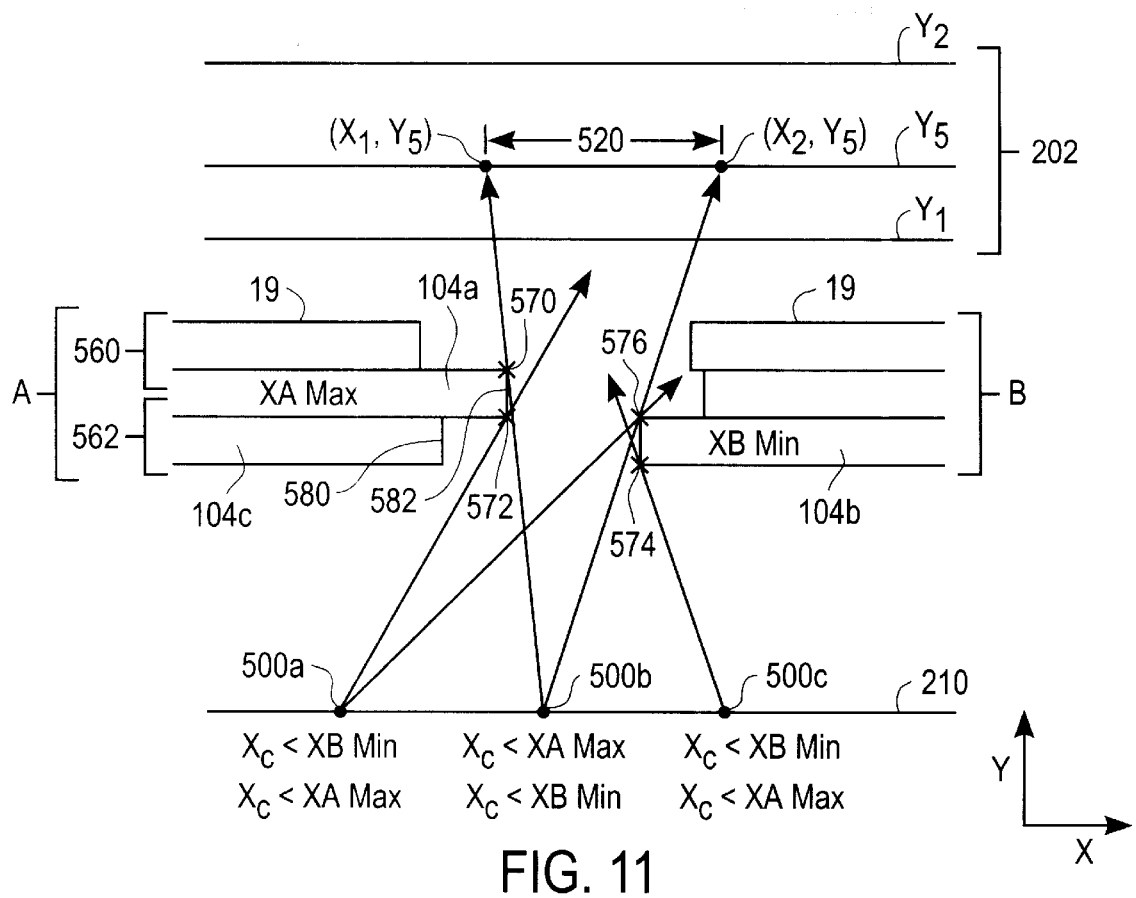
FIGS. 11–13 illustrate various ray tracings through various perspectives of a collimator.
Figure 12:
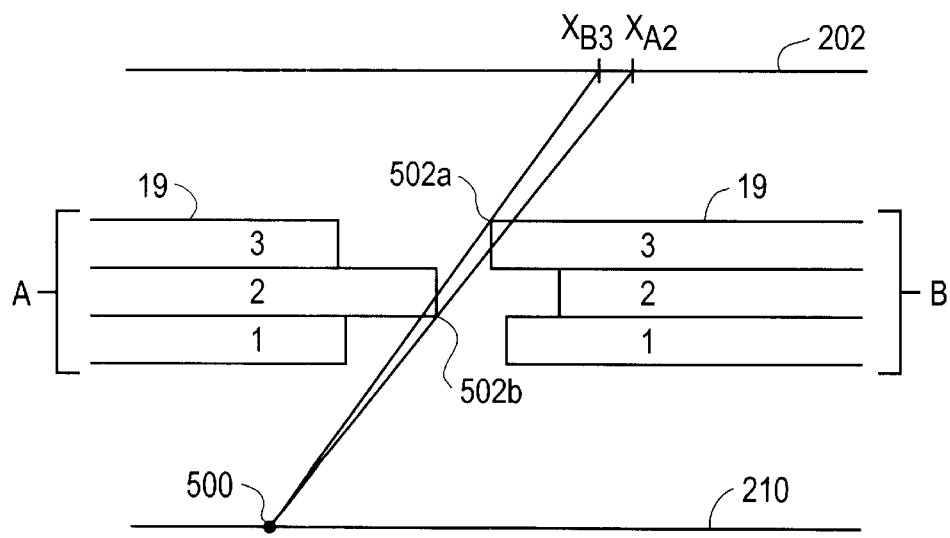

It is then determined whether $x_c$ of the calculation point is less than XAMAX (step 902). In the example shown in FIG. 11, the calculation point 500A is shown to have an $x_c$ less than XAMAX, while calculation points 500B and 500C are shown to have $x_c$ greater than or equal to XAMAX. If the $x_c$ of the current calculation point is not less than XAMAX, then the intersections with the radiation ray and the collimator leaves in the subset of collimator leaves of side "A" (as shown in the example of FIG. 11) are on the edges farther from the calculation point (step 904). For example, in FIG. 11, the calculation points 500B and 500C each have an $x_c$ which is shown to be greater than or equal to XAMAX. Accordingly, a ray traced from calculation points 500B and 500C would intersect an edge that is farther from $y_c$, such as edge 570, of the subset of collimator leaves of side "A".

If $x_c$ of the calculation point is less than XAMAX (step 902), then intersections with the ray and the collimator leaves of the subset of side "A" will be on the edge closer to the calculation point (step 906). For example, in FIG. 11, calculation point 500A is shown to have an $x_c$ less than XAMAX. Accordingly, a ray traced from calculation point 500A to scattering plane 202 intersects the subset of collimator leaves on the edges closer to the calculation point on the leaves on side "A". For example, the ray traced from calculation point 500A is shown to intersect with leaf 104A at the edge closer to the calculation point, such as edge 572.

It then determined whether $x_c$ is less than XBMIN (step 908). In the example shown in FIG. 11, the calculation points 500A and 500B are shown to have an $x_c$ which is less than XBMIN. If $x_c$ is greater than or equal to XBMIN, then the intersections with the ray traced from the calculation point to the scattering plane and the collimator leaves in the subset of side "B" of the collimator will be on the edges closest to the calculation point of the collimator leaves (step 910). For example, in FIG. 11, calculation point 500C is shown to have an $x_c$ greater than or equal to XBMIN. Accordingly, a ray traced from calculation point 500C to the scattering plane 202 intersects leaf 104B on the edge closer to the calculation point, such as edge 574.

If $x_c$ of the calculation point is less than XBMIN, then intersections with a ray traced from the calculation point to the scattering plane and the collimator leaves in the subset of side "B" of the collimator are on the edges farther from the calculation point (step 912). In the example shown in FIG. 11, calculation points 500A and 500B are shown to have $x_c$ less than XBMIN. A ray traced from these calculation points 500A and 500B to the scattering plane 202 is shown to intersect leaf 104B at an edge further from the calculation point, such as edge 576.

$X_1$ is then calculated for a given leaf (step 914). Since XA, $x_c$, $z_c$, and $z_s$ are all known, $x_1$ can be calculated from these known variables. $X_c$ has already been determined in step 420 of FIG. 10B; $z_c$ is a predetermined value, such as 100 cm (as shown in the example of FIG. 8 wherein calculation plane 210 is placed 100 cm below radiation source 17); and $z_S$ is also a predetermined number, such as 10 cm, (such as the $z_c$ shown in FIG. 8, wherein scattering plane 202 is placed 10 cm below radiation source 17).

XA is the x value for the intersection point at the appropriate edge of the given leaf under consideration, for which a value of $X_1$ is to be calculated. In the discussion related to step 900 of FIG. 17A, wherein the x values of the intersection points are calculated, the variable $x_i$ was used as a generic variable. XA is just the $x_i$ for the leaf under consideration on side A of the collimator. Similarly, the z value of that intersection point is required (in the discussion related to step 900 of FIG. 17A, the z value of the intersection point is generically labeled $z_i$, here it is referred to as ZA for consistency when referring to the z value of the leaf under consideration on side A of the collimator). Note that XA is not XAMAX, but XAMAX is related to the XA for the leaf that sticks out the most into the field.

Figure 17C:
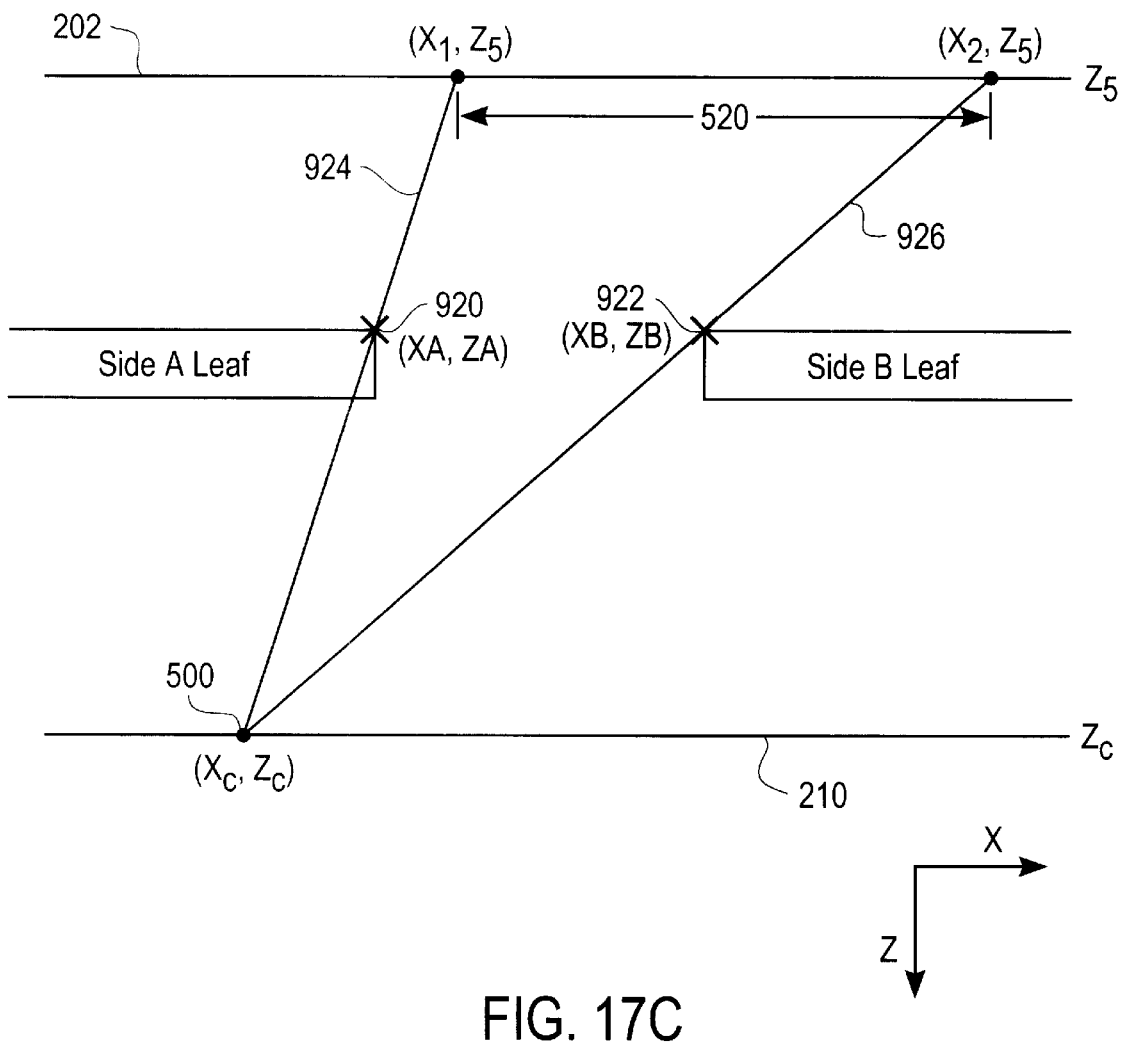
FIG. 17C is an illustration of an example of the method described in conjunction with FIGS. 17A–17B.

As shown in FIG. 17C, since $z_s$, ZA, XA, $z_c$, $x_c$ are all known at this point, $X_1$ can be determined by a linear equation. The points $(x_c, z_c)$ and (XA,ZA) determine a linear equation, and since the point $(X_1,z_s)$ lies on this line, putting $z_S$ into the linear equation allows one to solve for $X_1$. As implied by the example of FIG. 17C, the intersection points 920 and 922 ((XA, ZA) and (XB, ZB)) can be determined by solving for the intersection of the two linear equations that describe the ray being traced (924 and 926) and the edge of the leaf that is being intersected by the ray (e.g. points 504A–504D of FIG. 13). Note that ZA and ZB have previously been determined using the y-z plane view and the projections of these two linear equations onto the y-z plane, while XA and XB have been determined using similar triangles in the x-z plane. Using this information allows us to now solve for $X_1$. An example of such an equation is as follows:

$$X_1 = XA + (z_s - ZA)(XA - x_c)/(ZA - z_c)$$

Many variations of this equation may be used to vary the efficiency of the calculation. For example, a variation such as the following may also be used:

$$X_1 = x_c + d*c$$

where $d = z_s - z_c$ and can be calculated before entering the loops, and only $c = (XA - x_c)/(ZA - z_c)$ is calculated within the loops (not $X_1$ itself) and the value of c that would produce the maximum $X_1$ is used since $X_1$ only has to be calculated for the maximum condition (the one with the maximum value of c). (Note also that $(ZA - z_c)$ can be calculated before entering the loops which vary $x_c$ and save on redundant calculations.)

For the leaves on Side A, a unique value of $X_1$ can be determined for each leaf. That is, any given leaf on side A, if it were to be the only leaf to exist on that side, will block out scattered radiation, and thus it provides an $X_1$ limit on the scattering strip. If a ray was traced from a calculation point to the edge of the leaf (the edge that blocks the most radiation) and onto the scattering plane, $X_1$ would be the leftmost limit of the scattering strip that could contribute to radiation.

For all the leaves in side A, such an $X_1$ could be determined (pretending that each leaf were the only one existing), but only the maximum $X_1$ is needed, and this will be associated with the leaf on side A that blocks the most radiation from the left side of the scattering strip. In many cases this could be the leaf that sticks out furthest into the field, but not always.

The leaves on side A do not have an $X_2$ value associated with them. The reverse is true for the leaves on side B. $X_2$ may then be calculated for each given leaf on side B (step 916). $X_2$ may be calculated from XB, $x_c$, $z_c$ and $z_s$. Each leaf on side B can have an associated $X_2$ value, but only the minimum $X_2$ value is necessary for the calculation. There are no $X_1$ values associated with the leaves on side B. The values $X_1$ and $X_2$ are the limits of the scattering strip, and MIN $X_2$ (the smallest $X_2$ value calculated by pretending that each one of the leaves on side B was the only one that existed ) should be greater than MAX $X_1$ (the largest $X_1$ value calculated by pretending that each one of the leaves on side A was the only one that existed) for fluence contributions to be present.

$X_1$ is the x coordinate of the left edge of the scattering strip, and $X_2$ is the x coordinate of the right edge of the scattering strip. However, if a given leaf on side A were the only one to exist, it would determine $X_1$, and if a given leaf on side B were the only one to exist, it would determine $X_2$. Since there are many leaves on both side A and side B, the leaves that block the most radiation is desired to set the $X_1$ and $X_2$ properties of the scattering strip.

The $x_1$ and $x_2$ are then compared for all the leaves in the subset, and a maximum $x_1$ and a minimum $x_2$ are selected (step 918). Since it is desirable to have the $X_1$ property of the scattering strip to be from the leaf that blocks the most radiation on side A, the leaf that produces the maximum $X_1$ value among all the leaves on side A is selected. That maximum $X_1$ is now used to set the x coordinate of the left edge of the scatter strip. A similar process occurs for the leaves on side B and $X_2$, except that the minimum $X_2$ is needed, since the leaf on side B that has the minimum $X_2$ is the leaf that blocks the most radiation from the scatter strip and should be what is used to set the x coordinate of the right edge of the scattering strip. If the x coordinate of the left edge of the scattering strip is greater than or equal to the x coordinate of the right edge of the scattering strip, then no scattered radiation can come from that scatter strip and contribute fluence to the calculation point under consideration.

After the coordinates of the scatter strips on the scattering plane are found, the rectangular region of each scattering strip is projected onto the source plane and the coordinates of scatter squares on the source plane are determined from similar triangles, as previously described above in the identification of the coordinates of the scatter strips from locations on the calculation plane (see FIGS. 4 and 8). The ray trace continuation from the scatter strip in the scattering plane to a rectangular region in the source plane is done for every scatter strip so that the entire area that is projected onto the scattering plane is ultimately projected onto the source plane.

Figure 18:
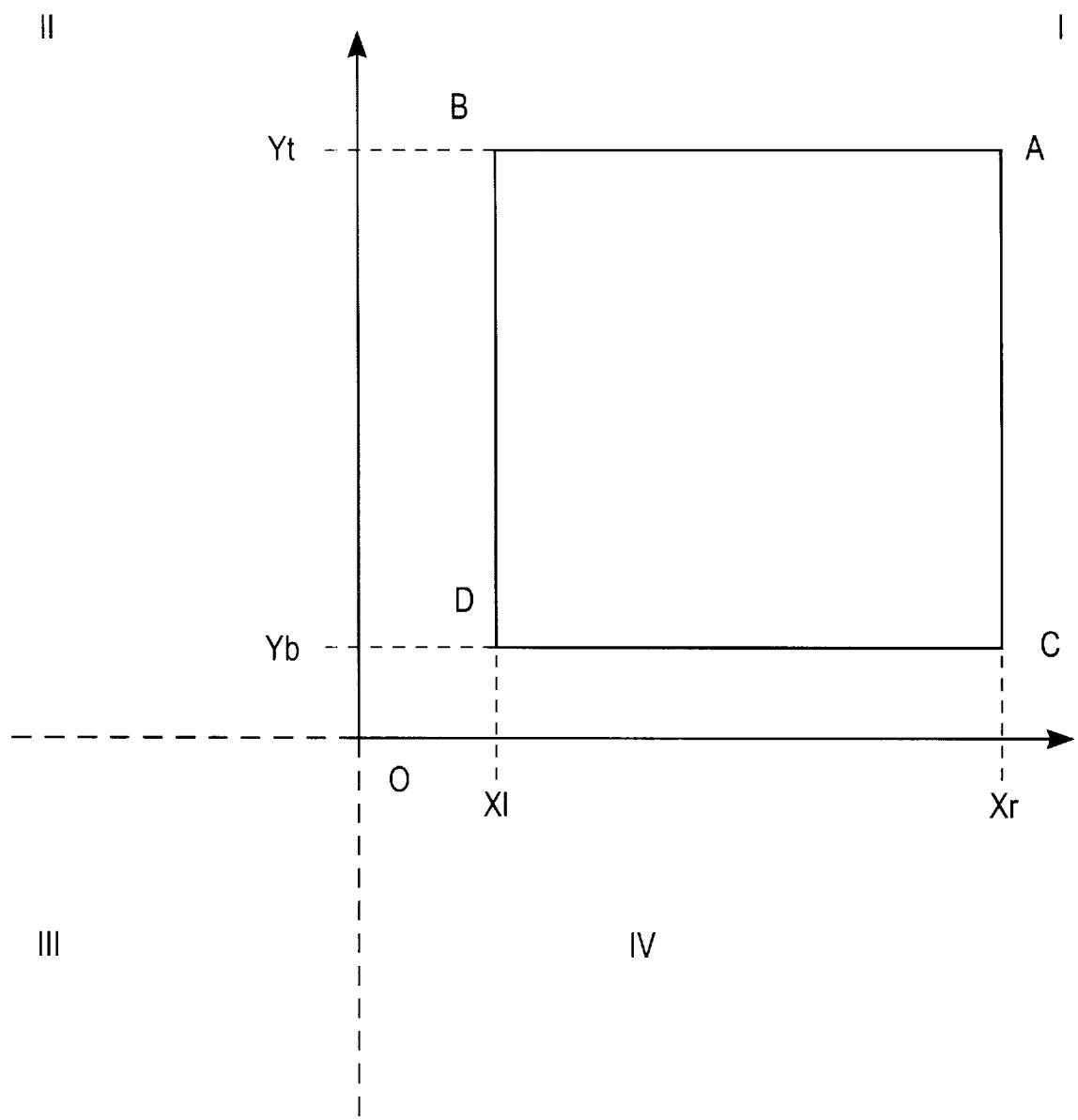
FIG. 18 is a scatter element projected from the scattering plane onto the source plane shown on a graph with an origin at an intersection point of the radiation beam with the source plane.

Since each scatter strip has a defined x1 and x2, a defined y coordinate ys, and the width of the scatter strip, ws, is also known (in the example given earlier it is 1 mm), the corners of the scatter strip have known coordinates (x1, ys+ws/2, zs), (x1, ys−ws/2, zs), (x2, ys+ws/2, zs), and (x2, ys−ws/2, zs). Hence a line from the calculation point under consideration (xc, yc,zc) to any one of the these corners can be extended to the source plane to find the corresponding coordinates for the projections of these corners in the source plane. Since the z coordinate for the projected corners in the source plane is the z coordinate for the location of the source plane (in FIG. 8 it would be zero), then, for each corner, only the x and y coordinates are unknown. Two linear equations can be solved for each corner, one being an equation in x and z to solve for the coordinate of the corner, while the other being an equation in y and z to solve for the y coordinate of the corner. Once this is done for all corners, the coordinates of the corners of the rectangular element on the source plane will be known and are shown in FIG. 18 as (xr,yt), (x1,yt), (xr,yb), (x1,yb). (The z coordinate is dropped for brevity since it is known that this is the z value of the source plane). Xr is determined from the linear equation solved from the points (xc,zc) and (x2,zs), while x1 is determined from the points (xc,zc) and (x1,zs). Yt is determined from the linear equation solved from the points (yc,zc) and (ys+ws/2, zs), while yb is determined from the points (xc,zc) and (ys−ws/2,zs). For each pair of points, the slope and intercept of the lines (using z as an independent variable) are determined and the corresponding value when z is at the source plane can be calculated from the linear equation.

The projected region bounded by these four projected corners in the source plane will span many source elements. In order to reduce the number of required calculations, rectangular regions that have one corner located at the intersection of the radiation beam with the source plane (defined as the origin) and the other corner at coordinates specified by indices of a lookup table are pre-integrated. The integral for any rectangular region can then be determined as a function of a lookup table values for the four corners of the rectangular region. This provides a finer grid for the source plane than that required for the scattering plane 202, thus resulting in fluence calculations with improved accuracy. The dimension of a side of a square element on the source plane 201 may be, for example, $\frac{1}{10}^{th}$ the size of the scatter element on the scattering plane. The elemental source area covered is $\frac{1}{100}^{th}$ of the elemental scatter area. The source elements on the source plane 201 preferably are squares whose sides have a length of approximately 0.1 mm to provide accurate calculations for source function integrations (e.g., with a source diameter of approximately 2 mm and scatter elements on the scattering plane of 1 mm squares).

FIG. 18 illustrates a projected rectangular region on the source plane identified with a right boundary at x=xr, a left boundary at x=x1, a top boundary at y=yt, and a bottom boundary at y=yb. The origin O is a point where the electron strikes the target in the source plane. The four corners of the scatter element are thus A=(xr, yt), B=(x1, yt), C=(x1, yb), and D=(xt, yb). If I(A), I(B), I(C), and I(D) are values of the integral based on a lookup table (described below) for the points A, B, C, and D, respectively, the result of integrating the function over the rectangle ABCD may be calculated as:

$$I(ABCD)=F(xr)F(yt)I(A)-F(x1)F(yt)I(B)-F(xr)F(yb)I(C)+F(x1)F(yb)I(D).$$

The functions F(x) and F(y) are either +1 or −1 based on a location of the point within the four quadrants of the graph shown in FIG. 18. For example, if a point is located in quadrant one, F(x) and F(y) will be +1; a point located in quadrant II will have an F(x) of −1 and F(y) of +1; a point located in quadrant III will have F(x) and F(y) equal to −1; and a point located in quadrant IV will have F(x) equal to +1 and F(y) equal to −1. The formula shown above for I(ABCD) therefor applies to a rectangular area located in any position relative to the origin on the source plane.

The values of I(A), I(B), I(C), and I(D) are found in a lookup table which contains preintegrated elements that have one corner at the origin and the other corner at the coordinates specified by the indices of the lookup table in units of the size of each source element. Within each memory location of the lookup table, a cumulative value indicating the fluence per element is stored.

Figure 19:
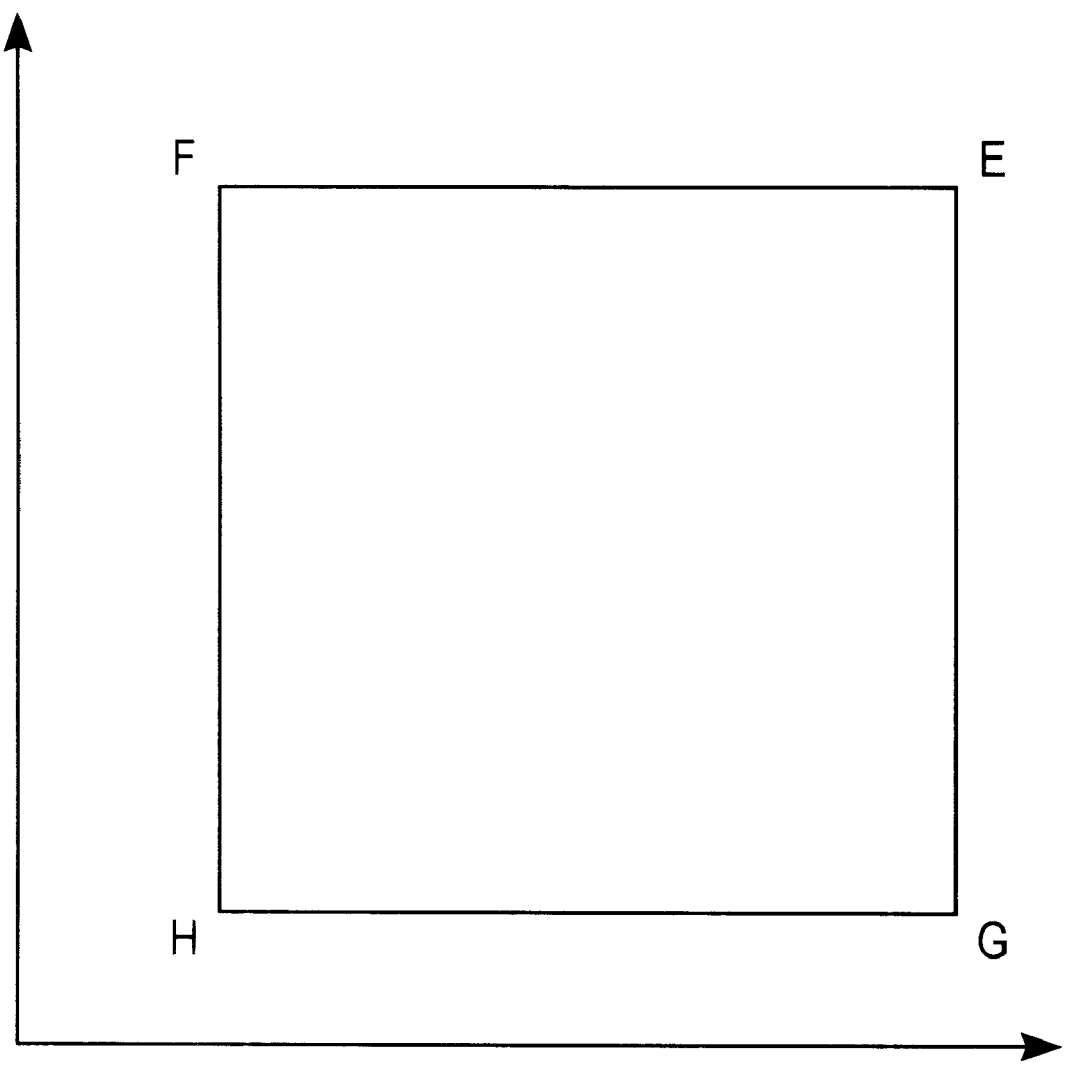
FIG. 19 is a source element illustrating an interpolation method for use with a lookup table.

Since a point may fall in between points that have values within the lookup table, it may be necessary to perform interpolation on the values within the table. For example, a point K may be located within a square having four corners E, F, G, and H as shown in FIG. 19 and defined as follows:

E=(xe, ye);
F=(xf, yf);
G=(xg, yg); and
H=(xh, yh).

The x dimension of the element is equal to xe−xf and the y dimension is equal to ye−yg. These dimensions are typically equal since the functions being modeled are radially symmetric. If K is defined as (xk, yk), then:

$$xh=xf \leq xk \leq xe=xg;$$

and $$yh=yg \leq yk \leq ye=yf.$$

Since the lookup table has values for T(E), T(F), T(G), and T(H) corresponding to points E, F, G, and H, respectively, the value for point K can be calculated as:

$$I(K)=T(H)+(xk-xh)[T(G)-T(H)]+(yk-yh)[T(F)-T(H)]+(xk-xh)(yk-yh)\{T(E)-T(G)-[T(F)-T(H)]\}.$$

The following describes a method for developing the lookup table. The coordinates of the lookup table are defined as:

$$T(i, j)=I(idx, jdy)$$

where:
dx=dimension in the x direction of the source element used for the integration;
dy=dimension in the y direction of the source element used for the integration;
idx=x coordinate of the point to be looked up;
jdy=the y coordinate of the point to be looked up.

Since the function is radially symmetric, the integral will also be radially symmetric so that:

$$T(i,j)=T(-i,j)=T(i,-j)=T(-i,-j).$$

Thus, only one quadrant needs to be stored in the lookup table. The table can be generated using the following recursion relations, (with the function to be integrated denoted by Φ):

$$T(i,j)=T(i, j-1)+Ts(i,j) \quad i,j=1, 2, \ldots, N$$

$$Ts(i,j)=Ts(i-1,j)+\tfrac{1}{4}dxdy[\Phi(idx,jdy)+\Phi(i-1)dx,jdy)+\Phi(idx,(j-1)dy)+\Phi((i-1)dx,(j-1)dy)] \quad i,j=1, 2, \ldots N$$

$$T(0,j)=T(i,0)=T(0,0)=Ts(0,j)=Ts(i,0)=Ts(0,0)=0$$

The table value T(i, j) represents the integral of the function over a rectangle with one corner at the origin and the other corner at the point (idx, jdy). The function Φ may be any radially symmetric function normalized so that its area integral over a disk with a radius R is equal to 1, and the value of Φ for points outside the disk is zero.

Figure 20:
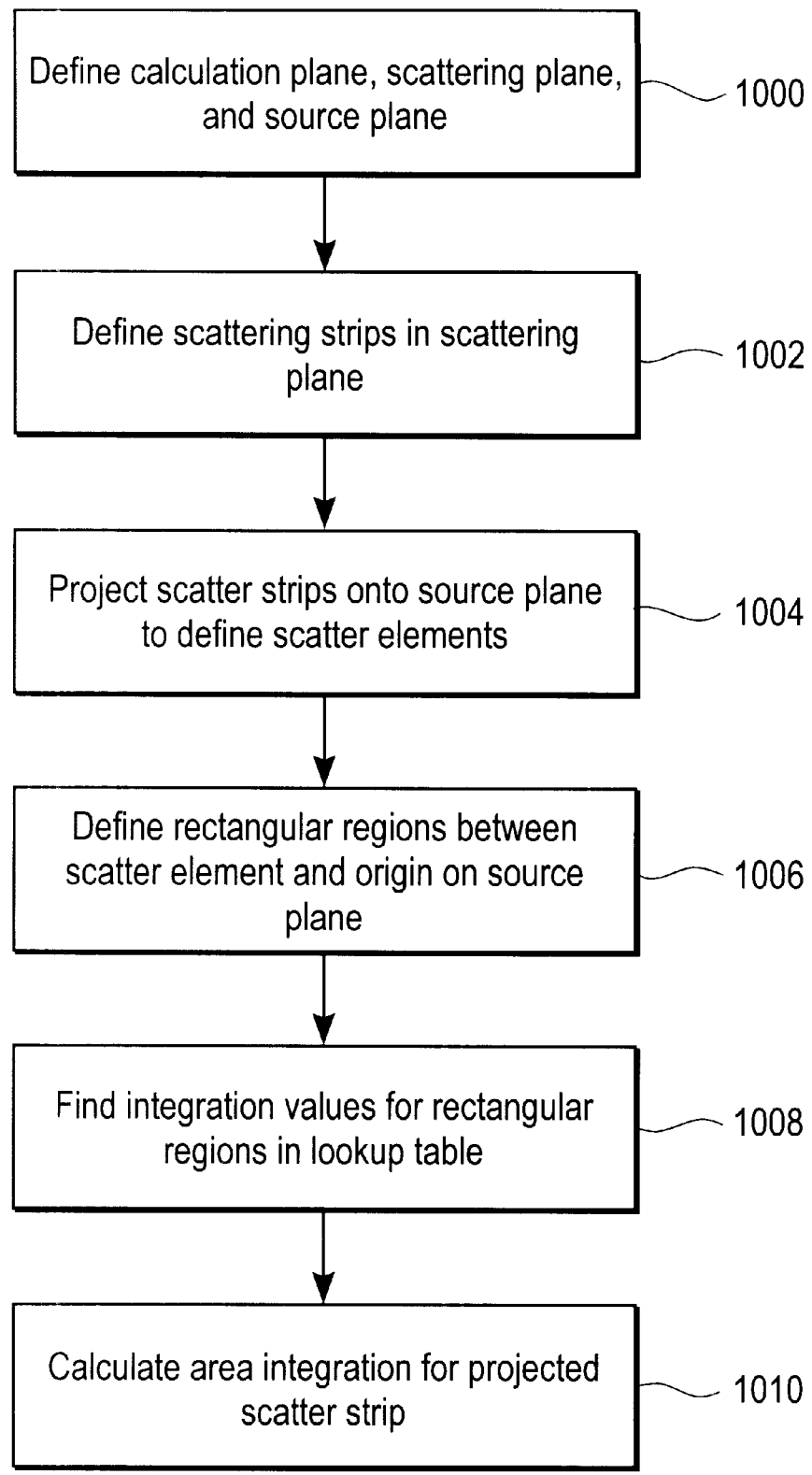
FIG. 20 is a flowchart illustrating a process for calculating scatter radiation.

FIG. 20 is a flowchart illustrating a process for calculating fluence contributions. At step 1000 a calculation plane, scattering plane, and source plane are defined. The scatter strips are then defined within the scattering plane for each point on the calculation plane (step 1002). Using ray tracing, the scatter strips are then projected from the scattering plane to the source plane (step 1004). An area integration is then performed for each projected scatter strip by defining rectangular regions between the corners of the projected scatter strip (corresponding to points A, B, C, and D of FIG. 18) and the origin (located at the intersection of the radiation beam with the source plane) (step 1006). The lookup table is used to find the area integration of each rectangular region (step 1008) and calculate a fluence value for each projected scatter strip (step 1010). Interpolation may be used if a coordinate of one of the regions is not provided in the table. The fluence values for each element are added together to determine the total fluence contributions.

Figure 21:
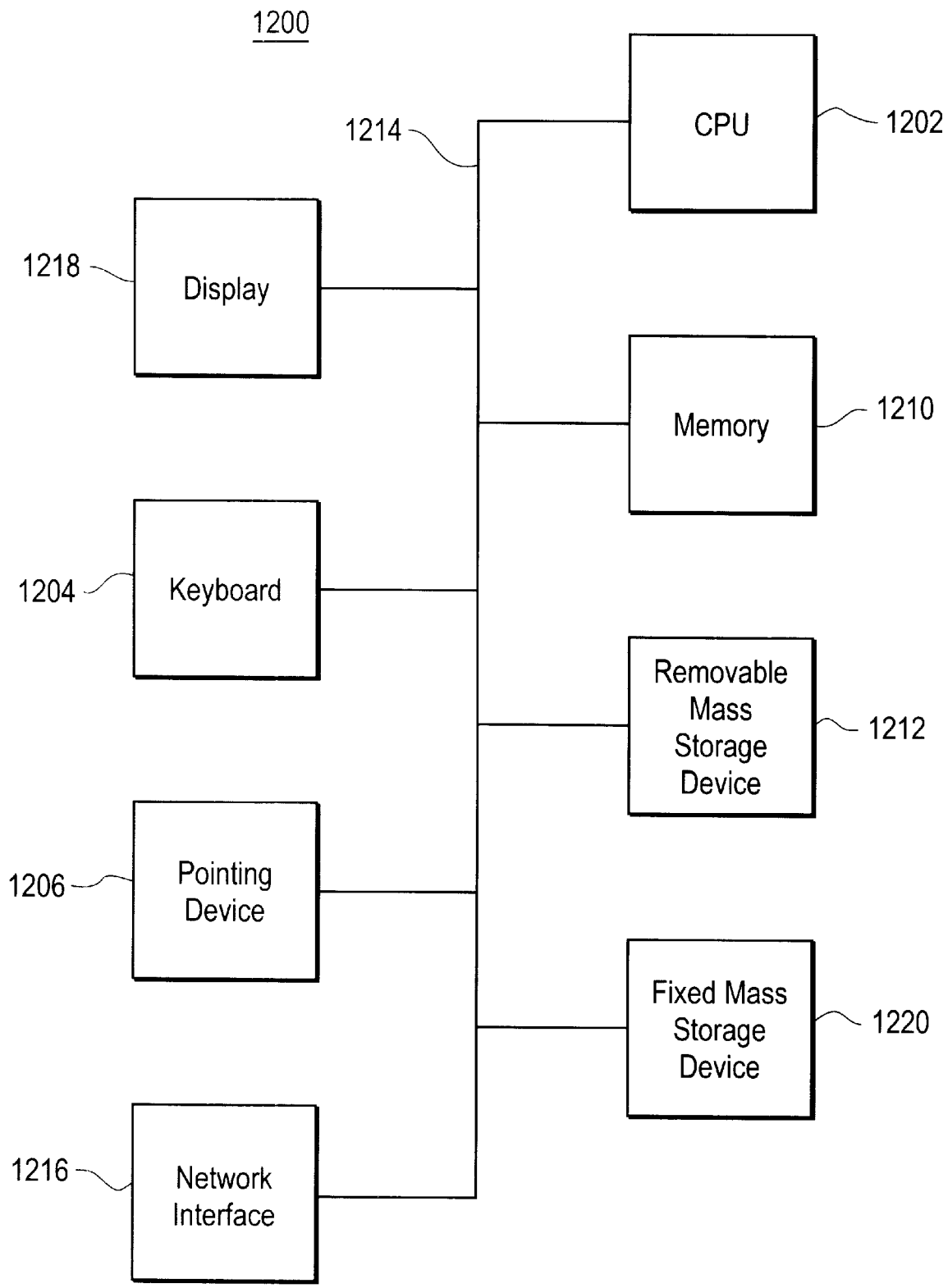
FIG. 21 is a block diagram of a computer suitable for implementing an embodiment of the present invention.

FIG. 21 is a block diagram of a general purpose computer system 1200 suitable for carrying out the processing in accordance with one embodiment of the present invention. FIG. 21 illustrates one embodiment of a general purpose computer system. Other computer system architectures and configurations can be used for carrying out the processing of the present invention. Computer system 1200, made up of various subsystems described below, includes at least one microprocessor subsystem (also referred to as a central processing unit, or CPU) 1202. That is, CPU 1202 can be implemented by a single-chip processor or by multiple processors. CPU 1202 is a general purpose digital processor which controls the operation of the computer system 1200. Using instructions retrieved from memory 1210, the CPU 1202 controls the reception and manipulation of input data, and the output and display of data on output devices.

CPU 1202 is coupled bi-directionally with memory 1210 which can include a first primary storage, typically a random access memory (RAW, and a second primary storage area, typically a read-only memory (ROM). As is well known in the art, primary storage can be used as a general storage area and as scratch-pad memory, and can also be used to store input data and processed data. It can also store programming instructions and data, in the form of data objects and text objects, in addition to other data and instructions for processes operating on CPU 1202. Also as well known in the art, primary storage typically includes basic operating instructions, program code, data and objects used by the CPU 1202 to perform its functions. Primary storage devices 1210 may include any suitable computer-readable storage media, described below, depending on whether, for example, data access needs to be bi-directional or uni-directional. CPU 1202 can also directly and very rapidly retrieve and store frequently needed data in a cache memory (not shown).

A removable mass storage device 1212 provides additional data storage capacity for the computer system 1200, and is coupled either bi-directionally or uni-directionally to CPU 1202. For example, a specific removable mass storage device commnonly known as a CD-ROM typically passes data uni-directionally to the CPU 1202, whereas a floppy disk can pass data bi-directionally to the CPU 1202. Storage 1212 may also include computer-readable media such as magnetic tape, flash memory, signals embodied on a carrier wave, PC-CARDS, portable mass storage devices, holographic storage devices, and other storage devices. A fixed mass storage 1220 can also provide additional data storage capacity. The most common example of mass storage 1220 is a hard disk drive. Mass storage 1212, 1220 generally store additional programming instructions, data, and the like that typically are not in active use by the CPU 1202. It will be appreciated that the information retained within mass storage 1212, 1220 may be incorporated, if needed, in standard fashion as part of primary storage 1210 (e.g. RAM) as virtual memory.

In addition to providing CPU 1202 access to storage subsystems, bus 1214 can be used to provide access other subsystems and devices as well. In the described embodiment, these can include a display monitor 1218, a network interface 1216, a keyboard 1204, and a pointing device 1206, as well as an auxiliary input/output device interface, a sound card, speakers, and other subsystems as needed. The pointing device 1206 may be a mouse, stylus, track ball, or tablet, and is useful for interacting with a graphical user interface.

The network interface 1216 allows CPU 1202 to be coupled to another computer, computer network, or telecommunications network using a network connection as shown. Through the network interface 1216, it is contemplated that the CPU 1202 might receive information, e.g., data objects or program instructions, from another network, or might output information to another network in the course of performing the above-described method steps. Information, often represented as a sequence of instructions to be executed on a CPU, may be received from and outputted to another network, for example, in the form of a computer data signal embodied in a carrier wave. An interface card or similar device and appropriate software implemented by CPU 1202 can be used to connect the computer system 1200 to an external network and transfer data according to standard protocols. That is, method embodiments of the present invention may execute solely upon CPU 1202, or may be performed across a network such as the Internet, intranet networks, or local area networks, in conjunction with a remote CPU that shares a portion of the processing. Additional mass storage devices (not shown) may also be connected to CPU 1202 through network interface 1216.

An auxiliary I/O device interface (not shown) can be used in conjunction with computer system 1200. The auxiliary I/O device interface can include general and customized interfaces that allow the CPU 1202 to send and, more typically, receive data from other devices such as microphones, touch-sensitive displays, transducer card readers, tape readers, voice or handwriting recognizers, biometrics readers, cameras, portable mass storage devices, and other computers.

In addition, embodiments of the present invention further relate to computer storage products with a computer readable medium that contain program code for performing various computer-implemented operations. The computer-readable medium is any data storage device that can store data which can thereafter be read by a computer system. The media and program code may be those specially designed and constructed for the purposes of the present invention, or they may be of the kind well known to those of ordinary skill in the computer software arts. Examples of computer-readable media include, but are not limited to, all the media mentioned above: magnetic media such as hard disks, floppy disks, and magnetic tape; optical media such as CD-ROM disks; magneto-optical media such as floppy disks; and specially configured hardware devices such as application-specific integrated circuits (ASICs), programmable logic devices (PLDs), and ROM and RAM devices. The computer-readable medium can also be distributed as a data signal embodied in a carrier wave over a network of coupled computer systems so that the computer-readable code is stored and executed in a distributed fashion. Examples of program code include both machine code, as produced, for example, by a compiler, or files containing higher level code that may be executed using an interpreter.

The computer system shown in FIG. 21 is but an example of a computer system suitable for use with the invention. Other computer systems suitable for use with the invention may include additional or fewer subsystems. In addition, bus 1214 is illustrative of any interconnection scheme serving to link the subsystems. Other computer architectures having different configurations of subsystems may also be utilized.

A method and system for calculating fluence contributions has been disclosed. Software written according to the present invention may be stored in some form of computer-readable medium, such as memory or CD-ROM, or transmitted over a network, and executed by a processor.

Although the present invention has been described in accordance with the embodiment shown, one of ordinary skill in the art will readily recognize that there could be variations to the embodiment and these variations would be within the spirit and scope of the present invention. Accordingly, many modifications may be made by one of ordinary skill in the art without departing from the spirit and scope of the appended claims.

What is claimed is:

1. A method for calculating fluence contributions for radiation delivery from a source to a treatment area through an aperture, the method comprising:

defining a calculation plane located adjacent to said treatment area and a scattering plane located between the radiation source and the calculation plane;

defining a source plane between the radiation source and the scattering plane;

ray tracing a point located on the calculation plane to the scattering plane to define a scatter strip;

projecting the scatter strip from the scattering plane to the source plane to define a rectangular region; and performing an area integration on said rectangular region to determine a fluence value for said rectangular region.

2. The method of claim 1 wherein performing an area integration comprises looking up predetermined values in a lookup table.

3. The method of claim 2 wherein the lookup table includes integration values for elements having a corner located at an origin defined by an intersection point of a radiation beam with the source plane.

4. The method of claim 1 further comprising calculating said predetermined values by integrating over an area from an origin defined by an intersection point of a radiation beam with the source plane.

5. The method of claim 1 wherein the scattering plane is divided into a plurality of sections and the scatter strip contains at least a portion of one of the plurality of sections.

6. The method of claim 5 wherein the scatter strip is related to a geometry of a collimator leaf.

7. The method of claim 1 wherein ray tracing a point located on the calculation plane comprises ray tracing a point through an aperture.

8. The method of claim 7 wherein said aperture is defined by collimator leaves.

9. The method of claim 1 further comprising determining whether a ray traced from said calculation point intersects a collimator leaf.

10. A system for calculating fluence contributions for radiation delivery from a source to a treatment area, the system comprising a processor configured to ray trace a point from a calculation plane located adjacent to said treatment area to a scattering plane to define a plurality of scatter strips, project the scatter strips onto a source plane located between the radiation source and scattering plane to define a plurality of rectangular regions corresponding to said plurality of scatter strips, and calculate area integrations for each of said rectangular regions, and a memory coupled with the processor and configured to provide instruction to the processor.

11. The system of claim 10 wherein the memory includes a lookup table comprising integration values for elements having a corner located at an origin defined by an intersection point of a radiation beam with said source plane.

12. The system of claim 10 wherein the scatter strip is related to a geometry of a collimator leaf.

13. The system of claim 10 wherein the processor is operable to determine whether a ray traced from said calculation point intersects a collimator leaf.

* * * * *